(12) United States Patent
Mamenta

(10) Patent No.: US 10,067,125 B2
(45) Date of Patent: Sep. 4, 2018

(54) SYSTEM AND METHOD FOR SPATIOTEMPORALLY ANALYZED RAPID ASSAYS

(71) Applicant: Edward L Mamenta, Brookline, MA (US)

(72) Inventor: Edward L Mamenta, Brookline, MA (US)

( * ) Notice: Subject to any disclaimer, the term of this patent is extended or adjusted under 35 U.S.C. 154(b) by 318 days.

(21) Appl. No.: 14/018,397

(22) Filed: Sep. 4, 2013

(65) Prior Publication Data
US 2014/0065647 A1    Mar. 6, 2014

Related U.S. Application Data

(60) Provisional application No. 61/743,415, filed on Sep. 4, 2012.

(51) Int. Cl.
    *G01N 33/558*      (2006.01)
    *G01N 33/543*      (2006.01)
    (Continued)

(52) U.S. Cl.
    CPC ..... *G01N 33/54306* (2013.01); *G01N 21/274* (2013.01); *G01N 21/8483* (2013.01); *G01N 21/85* (2013.01); *G01N 33/54386* (2013.01); *G01N 33/558* (2013.01); *B01L 2300/0825* (2013.01); *G01N 2021/8494* (2013.01)

(58) Field of Classification Search
CPC ............ G01N 33/558; G01N 21/8483; G01N 33/5091; G01N 2035/00108; G01N 33/53; G01N 33/5302; G01N 21/274; B01L 2300/0825; B01L 3/5023; B01L 2300/025; Y10S 435/805; Y10S 435/97
See application file for complete search history.

(56) References Cited

U.S. PATENT DOCUMENTS 5,464,749 A * 11/1995 Schwarzberg et al. ...... 435/7.92
5,753,517 A *  5/1998 Brooks et al. ................ 436/514
(Continued)

FOREIGN PATENT DOCUMENTS

EP            2385369 B1     2/2016
WO    WO 2014/039591 A1     3/2014

OTHER PUBLICATIONS

International Search Report of the International Search Authority for International Application No. PCT/US2013/058107, dated Dec. 12, 2013 by WIPO.
(Continued)

*Primary Examiner* — Erik B Crawford
(74) *Attorney, Agent, or Firm* — Daniel N. Smith

(57) ABSTRACT

The invention relates to methods of reliably and quantitatively determining the amount of an analyte of interest in a fluid sample using a flow-induced assay, such as an immunochromatographic assay, in which spatiotemporal measurements are recorded during the course of the assay reaction, generating a spatiotemporal dataset, and subsequently analyzed. The invention also relates to a system incorporating instruments for recording spatiotemporal datasets (spatiotemporal data recorders), devices comprised of flow-induced assays configured for analysis on a spatiotemporal recorder, and programs for analyzing the recorded spatiotemporal datasets.

6 Claims, 39 Drawing Sheets

(51) Int. Cl.
　　　　*G01N 21/85*　　　(2006.01)
　　　　*G01N 21/27*　　　(2006.01)
　　　　*G01N 21/84*　　　(2006.01)

(56) References Cited

U.S. PATENT DOCUMENTS

| | | |
|---|---|---|
| 2002/0142477 A1 | 10/2002 | Lewis et al. |
| 2004/0106211 A1 | 6/2004 | Kauer et al. |
| 2006/0073483 A1 | 4/2006 | White et al. |
| 2006/0246574 A1 | 11/2006 | Rosenstein et al. |
| 2006/0246599 A1* | 11/2006 | Rosenstein .......... G01N 33/558 436/514 |
| 2007/0161103 A1* | 7/2007 | Buchmann ................ B26F 1/12 435/287.2 |
| 2010/0196918 A1 | 8/2010 | Ellis et al. |
| 2010/0267065 A1* | 10/2010 | Geiger et al. .................. 435/13 |
| 2011/0229977 A1 | 9/2011 | Nishio et al. |
| 2012/0121466 A1 | 5/2012 | Potyrailo et al. |
| 2013/0203043 A1* | 8/2013 | Ozcan et al. ..................... 435/5 |

OTHER PUBLICATIONS

Written Opinion of the International Search Authority for International Application No. PCT/US2013/058107, dated Dec. 12, 2013 by the International Bureau of WIPO.
Extended European Search Report for European Patent Application No. 13835424.6, dated Jan. 25, 2016 by the European Patent Office.
European Intention to Grant for European Patent Application No. 13835424.6, dated Jun. 14, 2017, by the European Patent Office including approved application, claims, figures.

\* cited by examiner

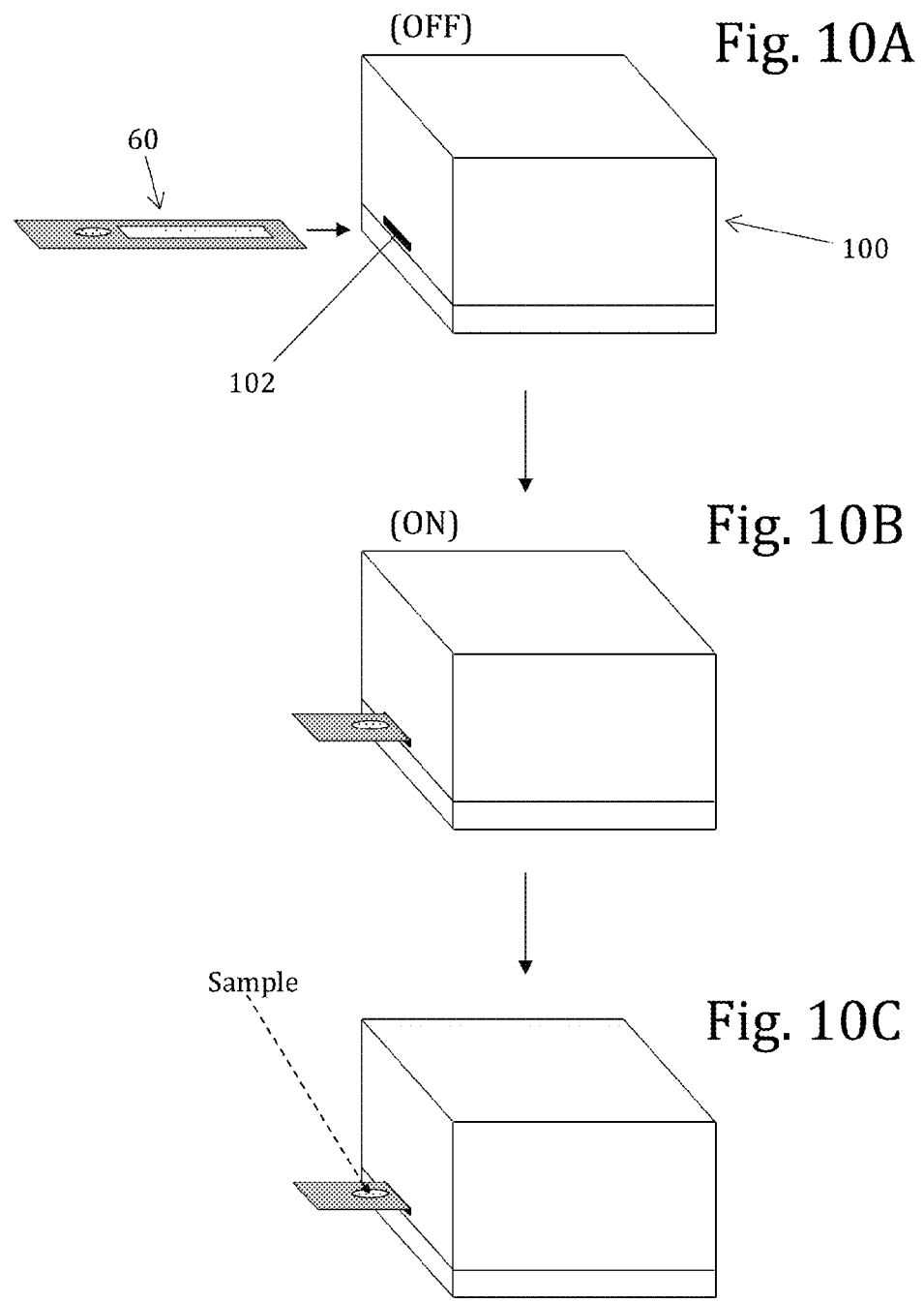

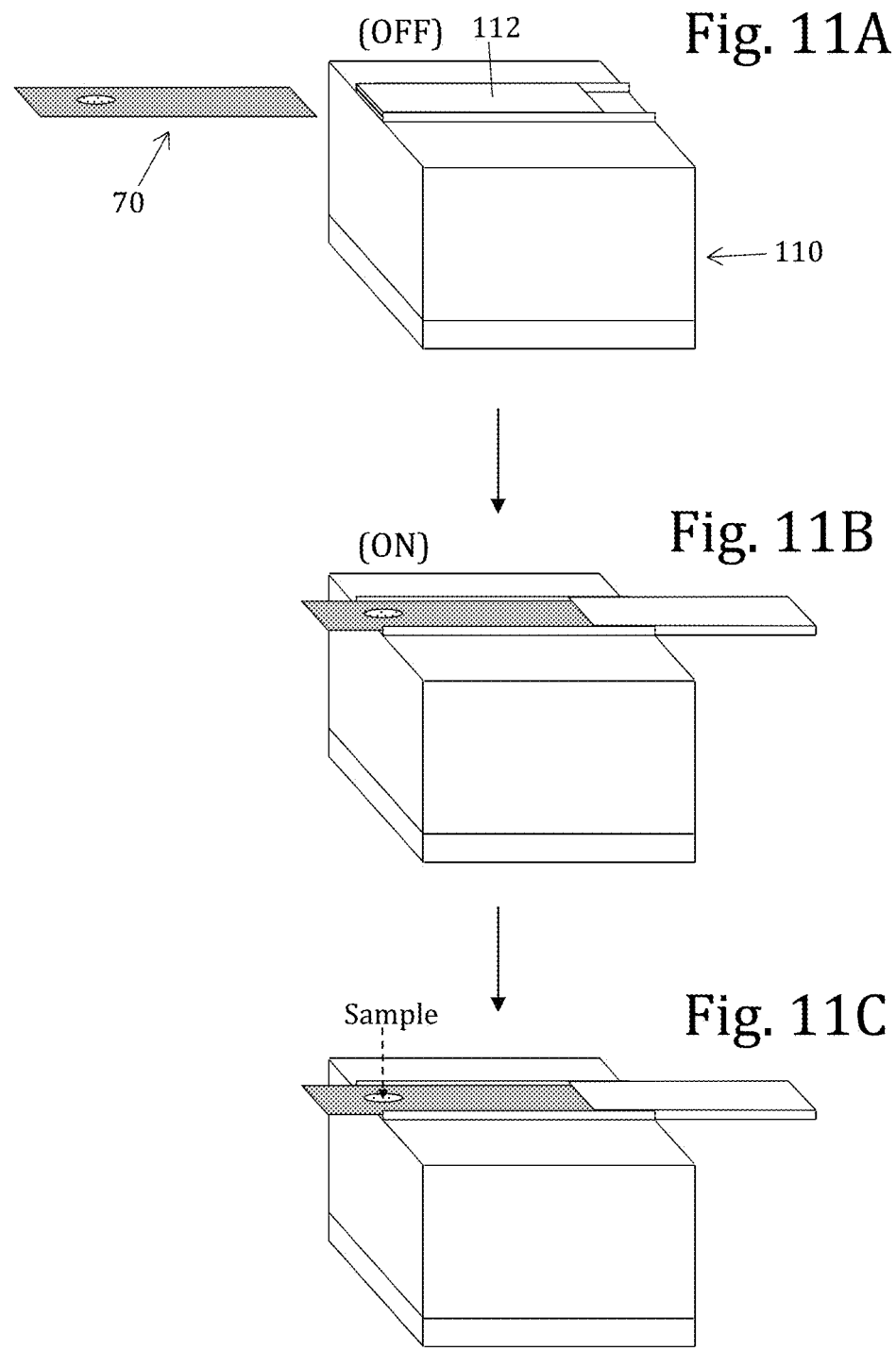

Fig. 12A
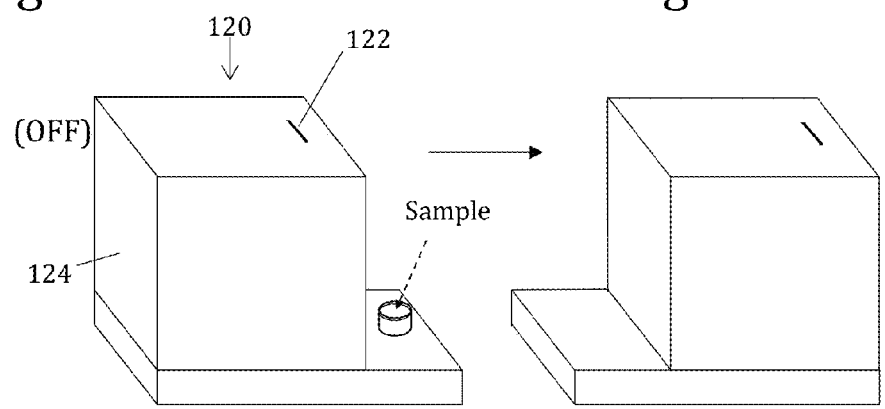
Fig. 12B
Fig. 12C
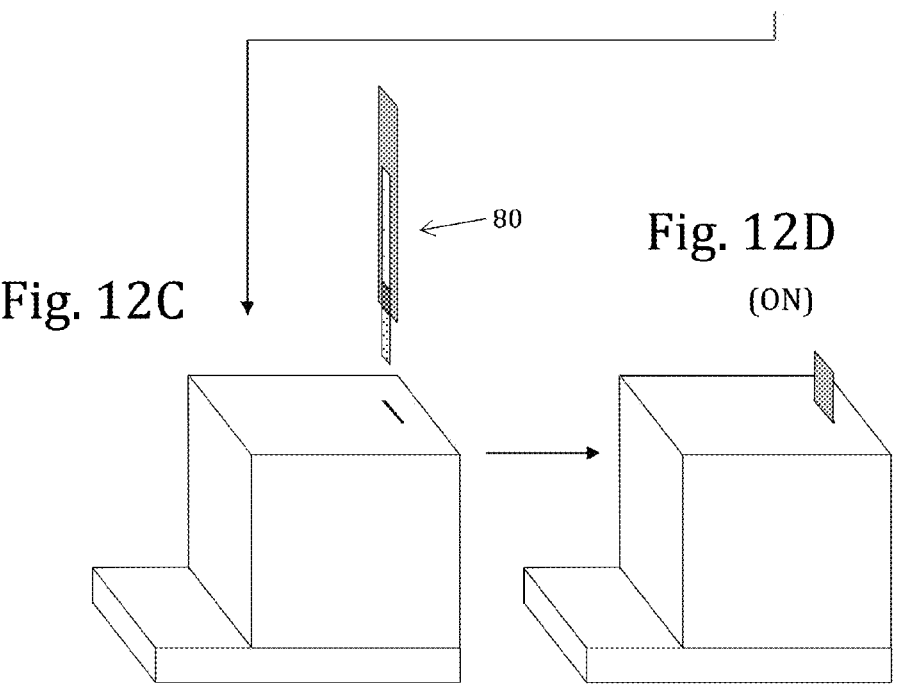
Fig. 12D
(ON)

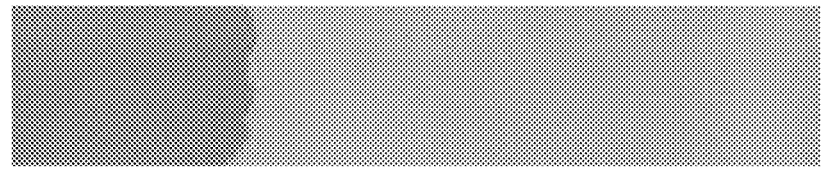

Fig. 17A

Subzone Number

| 3 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A |   |   |   |   |   |   |   |   |   |    |    |    |    |    |    |
| B |   |   |   |   |   |   |   |   |   |    |    |    |    |    |    |
| C |   |   |   |   |   |   |   |   |   |    |    |    |    |    |    |

Channel

Calculate average grayscale in each cell

Fig. 17B

TABLE 1 (Green Channel)   Subzone Number

| 3 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A | 166 | 166 | 166 | 166 | 184 | 209 | 210 | 210 | 210 | 210 | 210 | 210 | 210 | 211 | 211 |
| B | 164 | 165 | 165 | 166 | 187 | 209 | 210 | 209 | 210 | 210 | 210 | 210 | 210 | 211 | 211 |
| C | 166 | 166 | 166 | 166 | 194 | 208 | 210 | 210 | 210 | 210 | 210 | 210 | 210 | 211 | 211 |

Channel

TABLE 2 (Red Channel)

TABLE 3 (Blue Channel)

Fig. 18A

Subzone Number

| 3 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A | 166 | 166 | 166 | 166 | 184 | 209 | 210 | 210 | 210 | 210 | 210 | 210 | 210 | 211 | 211 |
| B | 164 | 165 | 165 | 166 | 187 | 209 | 210 | 209 | 210 | 210 | 210 | 210 | 210 | 211 | 211 |
| C | 166 | 166 | 166 | 166 | 194 | 208 | 210 | 210 | 210 | 210 | 210 | 210 | 210 | 211 | 211 |

Channel (row label)

Fig. 18B

Subzone Number

| 1 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A | 208 | 209 | 209 | 209 | 209 | 209 | 210 | 210 | 210 | 210 | 210 | 210 | 210 | 211 | 211 |
| B | 208 | 209 | 209 | 209 | 209 | 209 | 210 | 209 | 210 | 210 | 210 | 210 | 210 | 211 | 211 |
| C | 208 | 209 | 209 | 209 | 209 | 208 | 210 | 210 | 210 | 210 | 210 | 210 | 210 | 211 | 211 |

Subtract particle-containing image (3) from particle-free image (1).

Fig. 18C

Subzone Number

| 3 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A | 44 | 43 | 43 | 43 | 25 | 0 | 0 | 0 | 0 | 0 | 0 | 0 | 0 | 0 | 0 |
| B | 46 | 44 | 44 | 43 | 22 | 0 | 0 | 0 | 0 | 0 | 0 | 0 | 0 | 0 | 0 |
| C | 44 | 43 | 43 | 43 | 15 | 0 | 0 | 0 | 0 | 0 | 0 | 0 | 0 | 0 | 0 |

Subzone Number

| 3 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A | 44 | 43 | 43 | 43 | 25 | 0 | 0 | 0 | 0 | 0 | 0 | 0 | 0 | 0 | 0 |
| B | 46 | 44 | 44 | 43 | 22 | 0 | 0 | 0 | 0 | 0 | 0 | 0 | 0 | 0 | 0 |
| C | 44 | 43 | 43 | 43 | 15 | 0 | 0 | 0 | 0 | 0 | 0 | 0 | 0 | 0 | 0 |

Channel

Add up cells in each zone.

B

Subzone Number

| Total | 1 | 2 | 3 | 4 | 5 | 6 | 7 | 8 | 9 | 10 | 11 | 12 | 13 | 14 | 15 |
|-------|---|---|---|---|---|---|---|---|---|----|----|----|----|----|----|
| 3 | 134 | 130 | 130 | 129 | 62 | 0 | 0 | 0 | 0 | 0 | 0 | 0 | 0 | 0 | 0 |

Image No.

Fig. 20

Image / Channel — Subzone Number

| 3 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| A | 44 | 43 | 43 | 43 | 25 | 0 | 0 | 0 | 0 | 0 | 0 | 0 | 0 | 0 | 0 |
| B | 46 | 44 | 44 | 43 | 22 | 0 | 0 | 0 | 0 | 0 | 0 | 0 | 0 | 0 | 0 |
| C | 44 | 43 | 43 | 43 | 15 | 0 | 0 | 0 | 0 | 0 | 0 | 0 | 0 | 0 | 0 |

↓ Separate channels into individual tables.

Channel — Subzone Number

| A | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| Image No. 3 | 44 | 43 | 43 | 43 | 25 | 0 | 0 | 0 | 0 | 0 | 0 | 0 | 0 | 0 | 0 |

Subzone Number

| B | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| Image No. 3 | 46 | 44 | 44 | 43 | 22 | 0 | 0 | 0 | 0 | 0 | 0 | 0 | 0 | 0 | 0 |

Subzone Number

| C | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| Image No. 3 | 44 | 43 | 43 | 43 | 15 | 0 | 0 | 0 | 0 | 0 | 0 | 0 | 0 | 0 | 0 |

Fig. 21

Image Number, Subzone Number

| | 3 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Channel A | | 44 | 43 | 43 | 43 | 25 | 0 | 0 | 0 | 0 | 0 | 0 | 0 | 0 | 0 | 0 |
| B | | 48 | 47 | 47 | 47 | 28 | 0 | 0 | 0 | 0 | 0 | 0 | 0 | 0 | 0 | 0 |
| C | | 12 | 12 | 12 | 12 | 5 | 0 | 0 | 0 | 0 | 0 | 0 | 0 | 0 | 0 | 0 |

↓ Separate channels.

Channel, Subzone Number

| A | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Image No. 3 | 44 | 43 | 43 | 43 | 25 | 0 | 0 | 0 | 0 | 0 | 0 | 0 | 0 | 0 | 0 |

Subzone Number

| B | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Image No. 3 | 48 | 47 | 47 | 47 | 27 | 0 | 0 | 0 | 0 | 0 | 0 | 0 | 0 | 0 | 0 |

Subzone Number

| C | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Image No. 3 | 12 | 12 | 12 | 12 | 5 | 0 | 0 | 0 | 0 | 0 | 0 | 0 | 0 | 0 | 0 |

↓ Add up cells in similar channels.

Subzone Number

| (A,B) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Image No. 3 | 92 | 90 | 90 | 90 | 52 | 0 | 0 | 0 | 0 | 0 | 0 | 0 | 0 | 0 | 0 |

Subzone Number

| C | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Image No. 3 | 12 | 12 | 12 | 12 | 5 | 0 | 0 | 0 | 0 | 0 | 0 | 0 | 0 | 0 | 0 |

Fig. 22

Subzone Number

| Total | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 |
| 2 | 130 | 130 | 60 | 0 | 0 | 0 | 0 | 0 | 0 | 0 | 0 | 0 | 0 | 0 | 0 |
| 3 | 134 | 130 | 130 | 129 | 62 | 0 | 0 | 0 | 0 | 0 | 0 | 0 | 0 | 0 | 0 |

Image Number (rows); ⋮ final image

Channel

Subzone Number

| A | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 |
| 2 | 43 | 43 | 19 | 0 | 0 | 0 | 0 | 0 | 0 | 0 | 0 | 0 | 0 | 0 | 0 |
| 3 | 44 | 43 | 43 | 43 | 25 | 0 | 0 | 0 | 0 | 0 | 0 | 0 | 0 | 0 | 0 |

⋮ final image

Subzone Number

| B | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 |
| 2 | 43 | 43 | 19 | 0 | 0 | 0 | 0 | 0 | 0 | 0 | 0 | 0 | 0 | 0 | 0 |
| 3 | 46 | 44 | 44 | 43 | 22 | 0 | 0 | 0 | 0 | 0 | 0 | 0 | 0 | 0 | 0 |

⋮ final image

Subzone Number

| C | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 |
| 2 | 43 | 43 | 16 | 0 | 0 | 0 | 0 | 0 | 0 | 0 | 0 | 0 | 0 | 0 | 0 |
| 3 | 44 | 43 | 43 | 43 | 15 | 0 | 0 | 0 | 0 | 0 | 0 | 0 | 0 | 0 | 0 |

⋮ final image

Fig. 23    Subzone Number

| Image Number | Total | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 | 0 | 0 |
| 2 | 4 | 2 | 0 | 0 | 0 | 2 | 0 | 0 | 1 | 2 | 1 | 0 | 0 | 3 | 0 | 0 | |
| 3 | 94 | 2 | 0 | 0 | 2 | 2 | 1 | 0 | 1 | 1 | 2 | 2 | 2 | 0 | 1 | 3 | |
| 4 | 171 | 178 | 93 | 1 | 3 | 1 | 2 | 0 | 1 | 2 | 0 | 1 | 3 | 2 | 1 | 2 | |
| 5 | 162 | 148 | 162 | 183 | 15 | 4 | 1 | 3 | 2 | 1 | 2 | 1 | 3 | 2 | 2 | 1 | |
| 6 | 176 | 152 | 147 | 163 | 188 | 39 | 1 | 3 | 1 | 1 | 2 | 1 | 1 | 0 | 1 | 2 | |
| 7 | 173 | 163 | 152 | 151 | 169 | 182 | 40 | 3 | 1 | 2 | 2 | 2 | 2 | 1 | 3 | 1 | |
| 8 | 173 | 163 | 165 | 162 | 162 | 176 | 169 | 38 | 3 | 5 | 6 | 2 | 3 | 4 | 5 | 4 | |
| 9 | 165 | 153 | 155 | 166 | 163 | 160 | 175 | 150 | 20 | 4 | 1 | 1 | 1 | 3 | 1 | 1 | |
| 10 | 159 | 151 | 153 | 164 | 174 | 156 | 159 | 176 | 116 | 16 | 2 | 3 | 3 | 2 | 2 | 2 | |
| 11 | 158 | 145 | 148 | 163 | 178 | 162 | 155 | 164 | 170 | 90 | 5 | 3 | 3 | 2 | 3 | 3 | |
| 12 | 159 | 145 | 142 | 158 | 179 | 162 | 160 | 156 | 167 | 157 | 50 | 2 | 1 | 3 | 2 | 2 | |
| 13 | 162 | 142 | 143 | 156 | 183 | 152 | 158 | 159 | 158 | 172 | 137 | 18 | 4 | 3 | 1 | 1 | |
| 14 | 160 | 144 | 140 | 155 | 189 | 147 | 153 | 162 | 156 | 166 | 166 | 97 | 6 | 5 | 3 | 1 | |
| 15 | 163 | 142 | 141 | 153 | 191 | 140 | 144 | 156 | 160 | 158 | 172 | 163 | 42 | 4 | 0 | 2 | |
| 16 | 166 | 141 | 140 | 158 | 197 | 134 | 138 | 152 | 160 | 161 | 163 | 171 | 130 | 13 | 3 | 1 | |
| 17 | 164 | 141 | 139 | 160 | 203 | 130 | 130 | 143 | 151 | 163 | 163 | 164 | 169 | 75 | 4 | 1 | |
| 18 | 163 | 144 | 140 | 162 | 209 | 130 | 127 | 135 | 144 | 160 | 165 | 159 | 171 | 142 | 25 | 2 | |
| 19 | 159 | 142 | 143 | 162 | 216 | 126 | 124 | 132 | 141 | 156 | 166 | 165 | 165 | 164 | 92 | 5 | |
| 20 | 157 | 139 | 141 | 164 | 227 | 126 | 120 | 124 | 133 | 147 | 164 | 169 | 167 | 173 | 146 | 21 | |
| 21 | 153 | 132 | 140 | 165 | 231 | 125 | 117 | 123 | 127 | 142 | 159 | 169 | 167 | 168 | 163 | 77 | |
| 22 | 155 | 133 | 134 | 168 | 239 | 126 | 117 | 120 | 123 | 135 | 151 | 163 | 169 | 167 | 169 | 141 | |
| 23 | 159 | 131 | 132 | 167 | 247 | 124 | 116 | 119 | 121 | 129 | 142 | 159 | 172 | 167 | 174 | 164 | |
| 24 | 159 | 133 | 129 | 164 | 253 | 125 | 117 | 116 | 115 | 124 | 138 | 151 | 169 | 172 | 169 | 176 | |
| 25 | 160 | 135 | 129 | 158 | 259 | 123 | 111 | 115 | 114 | 120 | 132 | 143 | 159 | 173 | 173 | 177 | |
| 26 | 158 | 135 | 132 | 160 | 265 | 121 | 111 | 113 | 114 | 119 | 125 | 138 | 153 | 172 | 176 | 177 | |
| 27 | 160 | 132 | 133 | 163 | 269 | 117 | 109 | 110 | 112 | 116 | 122 | 131 | 149 | 164 | 179 | 180 | |
| 28 | 157 | 131 | 135 | 164 | 276 | 116 | 107 | 110 | 111 | 115 | 121 | 127 | 140 | 159 | 177 | 182 | |
| 29 | 157 | 135 | 132 | 166 | 279 | 113 | 105 | 109 | 110 | 113 | 117 | 125 | 138 | 152 | 171 | 186 | |
| 30 | 151 | 133 | 131 | 169 | 289 | 111 | 103 | 106 | 107 | 112 | 116 | 121 | 132 | 150 | 166 | 187 | |
| 31 | 149 | 131 | 132 | 166 | 293 | 113 | 98 | 105 | 108 | 110 | 115 | 121 | 128 | 139 | 161 | 182 | |
| 32 | 147 | 129 | 130 | 167 | 302 | 114 | 98 | 103 | 105 | 108 | 109 | 117 | 122 | 135 | 154 | 179 | |
| 33 | 144 | 126 | 131 | 169 | 306 | 114 | 96 | 100 | 101 | 108 | 112 | 116 | 122 | 132 | 148 | 174 | |
| 34 | 142 | 124 | 129 | 168 | 313 | 111 | 98 | 97 | 100 | 107 | 113 | 117 | 122 | 132 | 145 | 169 | |
| 35 | 138 | 122 | 128 | 171 | 315 | 112 | 98 | 94 | 98 | 105 | 111 | 114 | 119 | 127 | 141 | 166 | |
| 36 | 135 | 119 | 122 | 168 | 324 | 113 | 97 | 95 | 95 | 105 | 107 | 110 | 117 | 123 | 137 | 160 | |
| 37 | 129 | 114 | 120 | 166 | 329 | 113 | 95 | 97 | 96 | 100 | 108 | 112 | 115 | 124 | 137 | 158 | |
| 38 | 127 | 113 | 119 | 165 | 330 | 113 | 94 | 95 | 94 | 96 | 107 | 111 | 117 | 121 | 132 | 154 | |
| 39 | 125 | 110 | 114 | 164 | 335 | 110 | 93 | 94 | 92 | 98 | 103 | 110 | 113 | 120 | 131 | 150 | |
| 40 | 123 | 109 | 112 | 162 | 337 | 112 | 92 | 95 | 91 | 95 | 102 | 109 | 116 | 119 | 129 | 150 | |
| 41 | 124 | 107 | 112 | 161 | 342 | 109 | 92 | 93 | 92 | 98 | 100 | 107 | 113 | 120 | 128 | 147 | |
| 42 | 121 | 104 | 112 | 160 | 344 | 109 | 90 | 92 | 91 | 96 | 100 | 105 | 112 | 117 | 127 | 144 | |
| 43 | 122 | 103 | 106 | 157 | 349 | 109 | 91 | 91 | 90 | 94 | 96 | 103 | 110 | 114 | 124 | 145 | |
| 44 | 122 | 104 | 108 | 155 | 350 | 107 | 89 | 89 | 90 | 94 | 95 | 102 | 110 | 115 | 124 | 143 | |
| 45 | 120 | 105 | 104 | 156 | 352 | 106 | 88 | 89 | 88 | 93 | 96 | 100 | 110 | 114 | 121 | 142 | |
| 46 | 118 | 104 | 106 | 154 | 353 | 107 | 87 | 90 | 90 | 90 | 94 | 98 | 106 | 111 | 123 | 141 | |
| 47 | 116 | 104 | 106 | 154 | 358 | 103 | 86 | 86 | 87 | 91 | 94 | 94 | 101 | 111 | 120 | 139 | |
| 48 | 114 | 101 | 106 | 152 | 359 | 101 | 86 | 85 | 84 | 90 | 94 | 97 | 104 | 112 | 118 | 136 | |

Plot signal as a function of image number

Fig. 26

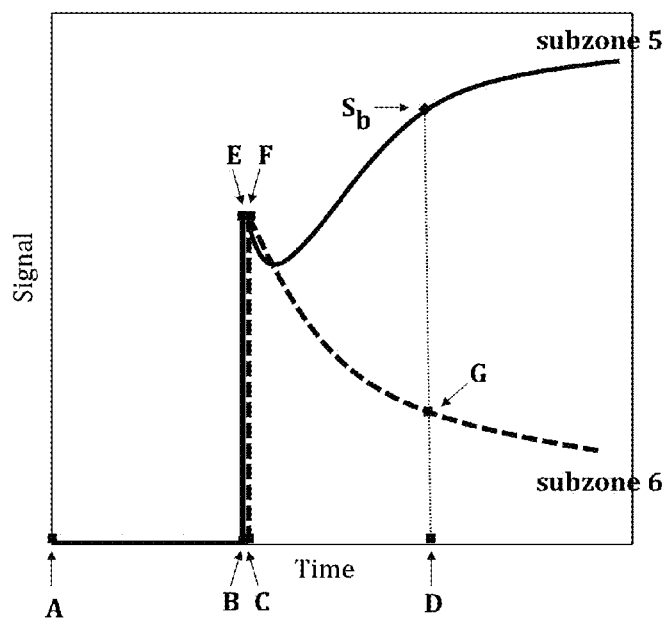

SPATIOTEMPORAL DATAPOINTS
$S_b$ = Binding signal at designated result
A = Time point when reaction begins (particles enter membrane)
B = Time point when particles enter subzone 5
C = Time point when particles enter subzone 6
D = Time point at designated result measurement
E = Initial concentration of particles in subzone 5
F = Initial concentration of particles in subzone 6
G = Final concentration of particles in subzone 6 (at designated result point)

ASSAY PARAMETERS
B minus A = Pre-incubation time
D minus B = Incubation time
F minus G = Relative total particles flowing through post-capture zone
(F minus G)/(D minus B) = Relative mean flow rate of assay reaction Fig. 27A
Fig. 27B
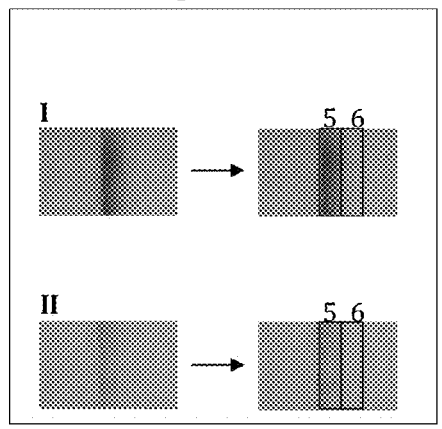
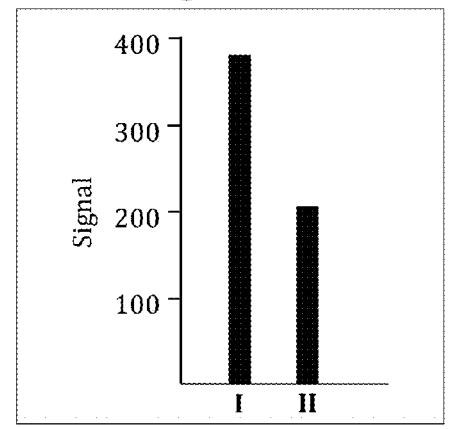
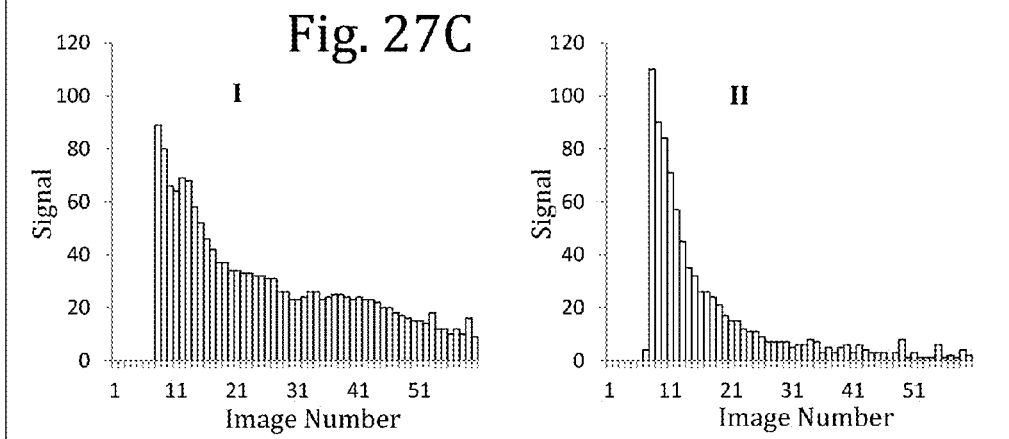
Fig. 27D
|  | I | II |
|---|---|---|
| B: Subzone 5 Signal ( at 5 min.) | 381 | 205 |
| C: Subzone 6 Signal (total) | 1612 | 853 |
| Ratio (B/C) | 0.24 | 0.24 |

Fig. 28A

INPUT

Data from Spatiotemporal Table

| B: Subzone 5 Signal ( at 5 min.) | 88 |
|---|---|
| C: Subzone 6 Signal (total) | 1599 |
| Signal (B/C) | 0.055 |

Fig. 28B

Stored Calibration Curve

| Conc. | Log[Conc.] | Signal (y) | Slope (m) | Y-Int. (b) |
|---|---|---|---|---|
| 0 | na | 0.24 | na | na |
| 2 | 0.30103 | 0.192 | -0.06867 | 0.212672 |
| 10 | 1 | 0.144 | -0.09966 | 0.243658 |
| 40 | 1.60206 | 0.084 | -0.07973 | 0.211726 |
| 160 | 2.20412 | 0.036 | na | na |

Fig. 28C

Find Slope and Y-Intercept:
m = -0.7973
b = 0.211726
Calculate Result:
RESULT = 10^((0.055- 0.211726)/-0.7973) = 92.4

OUTPUT = 92.4

SPATIOTEMPORAL DATAPOINTS
$S_b$ = Binding signal at designated result
A = Initial concentration of particles in subzone 5 – subzone 17
B = Final concentration of particles in subzone 5 – subzone 17 (at designated result point)

TEST STRIP PROTOCOL PARAMETERS
B = Final concentration of particles in subzone 5 – subzone 17 (at designated result point)

Fig. 31A
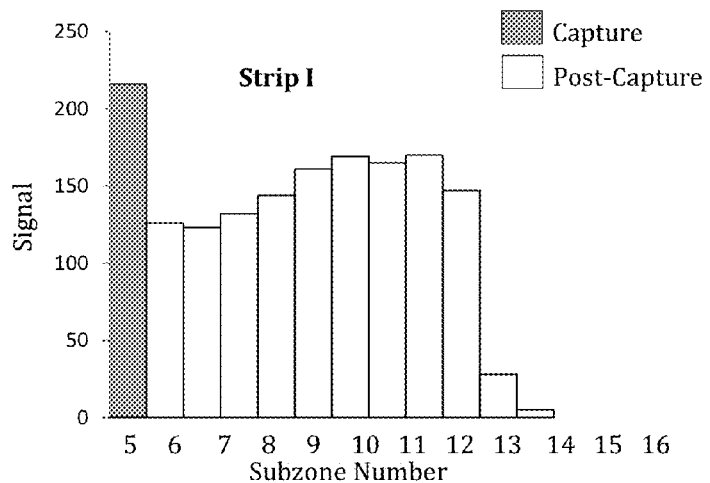
Fig. 31B
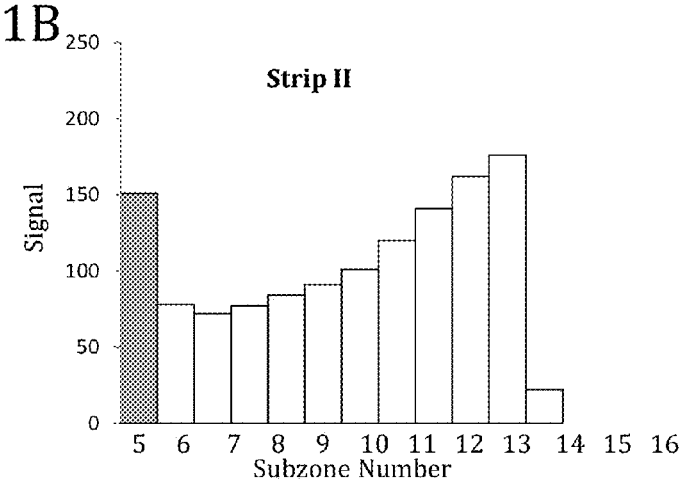
Fig. 31C
|  | I | II |
|---|---|---|
| Capture Zone Signal (Zone 5 minus Zone 6) | 90 | 73 |
| Post-Capture Zone Signal (Total Subzones) | 1375 | 1124 |
| Ratio (Capture/Post-Capture) | 0.066 | 0.065 |

Fig. 32A

INPUT
Data from Spatiotemporal Table

| B: Subzone 5 Signal ( at 2 min.) | 26 |
|---|---|
| C: Post-Capture Zone (total subzones) | 136 |
| Signal (B/C) | 0.019 |

Fig. 32B

Stored Calibration Curve

| Conc. | Log[Conc.] | Signal (y) | Slope (m) | Y-Int. (b) |
|---|---|---|---|---|
| 0 | na | 0.065 | na | na |
| 2 | 0.30103 | 0.052 | -0.02046 | 0.058158 |
| 10 | 1 | 0.038 | -0.01943 | 0.057133 |
| 40 | 1.60206 | 0.026 | -0.01943 | 0.057133 |
| 160 | 2.20412 | 0.014 | na | na |

Fig. 32C

Find Slope and Y-Intercept:
m = -0.01943
b = 0.057133
Calculate Result:
RESULT = 10^((0.019 - 0.057133)/-0.01943) = 91.7

OUTPUT = 91.7

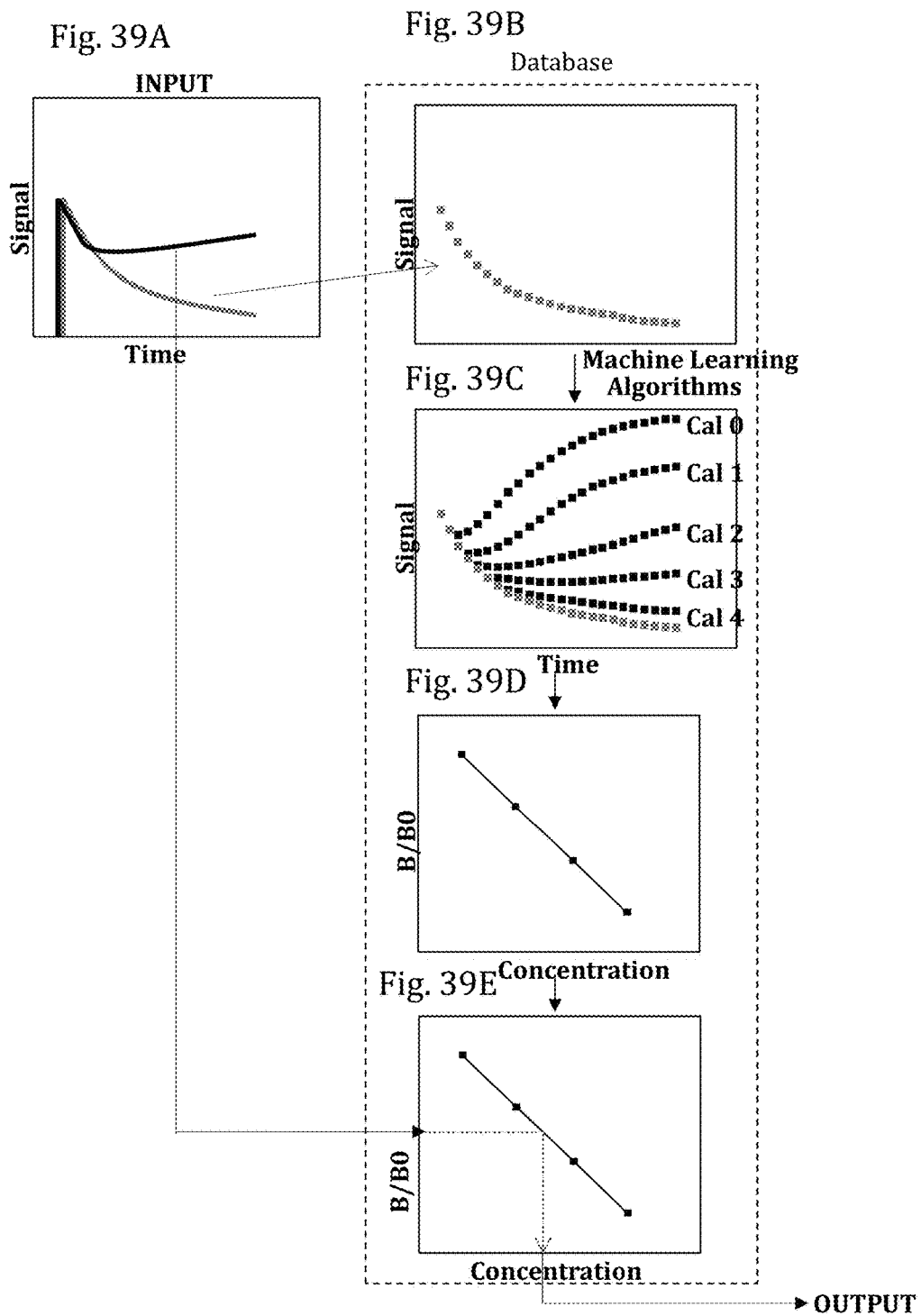

SYSTEM AND METHOD FOR SPATIOTEMPORALLY ANALYZED RAPID ASSAYS

CROSS REFERENCE TO RELATED APPLICATION

This application claims the benefit of U.S. Provisional Patent Application No. 61/743,415 filed on Sep. 4, 2012, the contents of which are incorporated herein by reference.

FIELD OF THE INVENTION

The present invention relates to a reliable, rapid, quantitative diagnostic test system and method suitable for on-site determination of analytes in fluid samples.

BACKGROUND OF THE INVENTION

Rapid immunochromatographic assay devices (also referred to herein simply as "rapid assay devices") are currently available to test clinical samples (e.g. whole blood, serum, plasma, urine, saliva) for a wide variety of analytes, such as hormones, drugs, toxins, metabolites, cardiac markers, and pathogen-derived antigens. In addition, rapid assay devices are also used extensively in non-clinical applications such as food and environmental testing. Typical devices are comprised of an immunochromatographic assay strip contained within a housing that exposes selective portions of the strip, while at the same time concealing the majority of this strip component. FIG. 1A shows a typical device 10 that includes a plastic housing 12, containing an assay strip, which is accessed through a sample receiving port 14, and viewable through one or more windows that expose the test zone 16, and the control zone 18. FIG. 1B shows the position of the assay strip 11 within the housing. In an exemplary implementation of the device, a fluid sample is applied to the sample receiving port and a period of time is allowed to elapse before viewing the results in the test and control windows. FIG. 1C shows a typical test result, in which a visible line forms inside the test and control windows (13 and 15, respectively). The band forms from a reaction process that occurs following application of sample to the device. This process typically creates in interim discoloration on the strip prior to the final viewed result. This interim state is disregarded with respect to interpreting the result. Indeed, many test protocols direct the user to avoid observing the interim discolored state to prevent difficulties with interpreting the final result.

Most rapid assay devices are designed for simple qualitative analysis, indicating either the presence or absence of an analyte at a particular cut-off level, based on a visual interpretation of band formation. For sandwich assays, the presence of an analyte in a sample is indicated by the formation of a line in the test zone, whereas for competition assays the presence of an analyte in a sample is indicated by the absence of a line forming in the test zone. The presence of the control line typically indicates that the assay has been correctly performed to completion. Inspection of the test and control zones occurs only after sufficient time has elapsed to allow for optimal viewing (typically 5-10 minutes following sample application). During this incubation period an immunochromatographic reaction is initiated, propagated and completed by the fluid sample migrating through the assay strip (via capillary action) and interacting with a series of reagents bound reversibly or irreversibly to the strip. Such reagents may include an analyte-specific binding pair (e.g. an antibody or antigen) coated onto labeled test particles, and an analyte-specific binding pair coated within the test zone.

Because rapid assay devices are simple to perform and can be interpreted visually without the aid of instrumentation, they are widely used for obtaining quick test results outside of laboratory settings (usually at the site of sample collection), thus providing a convenient alternative to transporting these samples to a laboratory for analysis. However, the advantages of these devices are offset by the fact that they are considerably less reliable than alternative laboratory-based immunoassays, and generally unable to provide quantitative results. Laboratory immunoassays (such as those performed on automated analyzers or with ELISA kits) incorporate precisely defined and controlled assay conditions. These conditions involve such aspects as the concentration or molar ratio of sample components to reagent components, the reaction volumes, and the reaction incubation times. Calibrator and control samples are also incorporated as part of the standard laboratory protocol and performed under the same conditions as the test samples. Deviation from the defined assay conditions can result in erroneous test results. In a laboratory setting this deviation is avoided with the use of sophisticated instrumentation, trained personnel and strict operating procedures.

In contrast to laboratory-based immunoassays, rapid assay devices are highly limited in their ability to deliver defined assay conditions, as these conditions are dictated by various flow dynamics that cannot be precisely replicated on each device. The assay reaction is induced by the application of fluid sample onto the strip, where it initially encounters reversibly bound test particles. As capillary action moves the sample through the strip, the test particles are rehydrated and mobilized. The rate at which the particles mobilize, total number of particles mobilized, and direction of particle migration across the strip, collectively contribute to the concentration and molar ratio of active reagent molecules to analyte molecules. As the sample and particles continue to flow along the strip, they eventually come in contact with the test zone where a second set of reagents is immobilized. The time required to reach the test zone, and the rate at which the sample and particles flow through the test zone, effectively define the assay incubation times. Thus, the assay conditions of a typical rapid assay device are largely governed by flow dynamics, which are in turn governed by properties of the test device that cannot be precisely reproduced for each individual device, resulting in device-to-device variation in assay conditions. Such properties of the device include membrane porosity, contact forces between membranes, and adhesion forces between the membrane and embedded test particles.

Attempts have been made to improve rapid test reliability by incorporating photo-optic reading instruments that measure and analyze color intensity of the test band. While this approach allows the test band to be analyzed with greater objectivity and quantitation (compared with visual interpretation), it fails to address the underlying problem of variable flow dynamics that can non-specifically influence the intensity of test band formation. Other approaches have focused on using the intensity of the control line to normalize the results of the test band. This approach does incrementally improve reliability and quantitation; however, the results still remain far inferior to laboratory-based systems. In addition, the control line approach requires considerably greater manufacturing effort compared to that of a standard rapid assay device and introduces additional variables that can compromise the interpretation of test results.

There remains a compelling need to develop a rapid assay system that can be performed on-site (outside of a laboratory setting) yet provide results with reliability and quantitation comparable to a laboratory-based system. The current invention is based on the surprising finding that reliable and quantitative rapid assays, suitable for on-site applications, can be developed using immunochromatographic components, despite the fact that assay conditions cannot be precisely controlled with such components.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The invention relates to methods of reliably and quantitatively determining the amount of an analyte of interest in a fluid sample using a flow-induced assay, such as an immunochromatographic assay, in which spatiotemporal measurements are recorded during the course of the assay reaction and subsequently analyzed. The invention also relates to devices comprised of flow-induced assays configured for spatiotemporal analysis, instruments for recording spatiotemporal datasets (spatiotemporal data recorders), and analysis programs for analyzing spatiotemporal datasets.

For an immunochromatographic assay, the methods use a device incorporating a membrane strip made of a suitable material, such as cellulose nitrate or glass fiber, which has sufficient porosity and the ability to be wet by the fluid containing the analyte, and which allows movement of particles by capillary action. The membrane strip has an application region, a particle region and a test area, with the test zone being further sub-divided into a measurable pre-capture zone, a measurable capture zone, and a measurable post-capture zone. The capture zone is between the pre-capture zone and the post-capture zone. The membrane strip may be comprised of a single piece of material or multiple overlaid pieces of material. The strip may also incorporate an inert back support made of a suitable material, such as plastic. In some embodiments, the device is comprised of the strip alone, while in other embodiments the device is comprised of the strip contained within a housing designed to allow for fluid sample application and measurement of the test zone.

Imbedded in the particle region of the device is a population of test particles such as colloidal gold particles or organic polymer latex particles. The test particles are coated with a binding reagent comprised of either an antibody to the analyte, an analog to the analyte, or the analyte, itself. The particles can be labeled, using a colorimetric, fluorescent, luminescent, or other appropriate label, to facilitate detection. The capture zone is coated with a capture reagent comprised of either an antibody to the analyte, an analog to the analyte, or the analyte, itself.

In the methods, the application region of the assay device is contacted with the fluid sample to be assayed for the analyte of interest. The membrane strip is then maintained under conditions which are sufficient to allow capillary action of fluid to transport the analyte of interest, if analyte is present in the sample, through the application region to the particle region. The apparatus is further maintained so that when analyte of interest reaches the particle region, the analyte binds to any analyte binding reagent coated on the test particles imbedded in the particle region. Test particles, including those which are bound with analyte, are mobilized by sample fluid and move by capillary action through the pre-capture zone of the strip to the capture zone. The capture reagent interacts with analyte-bound test particles, analog-bound test particles or analyte-free antibody-bound test particles, depending on the nature of the assay (i.e. sandwich or competitive); binding interactions between the capture reagent and the test particles result in arrest of test particles in the capture zone, while test particles that do not undergo binding interactions in the capture zone continue to migrate past the capture zone into the post-capture zone. It should be noted that the amount of binding that occurs in the capture zone is a function of a) the amount of analyte of interest in the fluid sample, and b) the cumulative effect of the flow-induced assay dynamics, including the rate at which test particles mobilize from the particle zone, the time between particle mobilization and entry into the capture zone, the flow rate and concentration of particles through the capture zone, and the total number of particles migrating through the capture zone.

The method further involves subjecting the immunochromatographic assay device to spatiotemporal measurements prior to sample application and throughout the course of the assay reaction. To accomplish this, the device is constructed so that the test particles are accessible to measurement at each stage of the reaction, including the initial mobilization from the particle region and migration from the particle region to, sequentially, the pre-capture zone, the capture zone, and the post-capture zone. Spatiotemporal measurements are collected with a spatiotemporal data recorder. In a preferred embodiment the recorder incorporates a digital camera capturing a succession of digital images over time. These digital images encompass the pre-capture zone, the capture zone, and the post-capture zone, at defined time intervals throughout the assay reaction period. Each recorded image is composed of a two-dimensional grid of picture elements or pixels, with each pixel corresponding to an intensity value proportional to the number of test particles present at a defined location on the strip (i.e. an associated spatial value). In other embodiments, a single spatial value may be defined by the sum or average of multiple pixels encompassing a given area of the image. With successive images, the intensity at each pixel is also defined over time (i.e. an associated temporal value). Collectively, these values comprise a "spatiotemporal dataset" of the assay reaction. The spatiotemporal dataset recorded from the reacted immunochromatographic assay device supplies information that can be used to reliably and quantitatively determine the amount of the analyte of interest in the applied fluid sample.

The method further involves performing an analysis of the spatiotemporal dataset to determine the amount of analyte present in the applied fluid sample. Broadly speaking, the analysis uses data recorded from the pre-capture zone, and post-capture zone to define the precise assay conditions under which test particle binding occurs in the capture zone. These precisely defined assay conditions are then used in conjunction with the data recorded from the capture zone to define the specific effect of sample analyte on the capture zone data, thus allowing for a calculation of analyte present in the sample. The analysis may also include comparing the spatiotemporal dataset of the test sample with one or more spatiotemporal datasets recorded from calibrator samples. In a preferred embodiment, the analysis is performed by a software program. The software program may be contained on a computer connected directly or wirelessly to the spatiotemporal recorder. Alternately, the software program may be contained on a computer at a location separate from the site of the spatiotemporal data recorder (i.e. an off-site computer). In this circumstance, some or all of the spatiotemporal dataset would be transported to the off-site computer for analysis. In a preferred embodiment, the method of transport would be through an internet connection. Results of the analysis could then be transported back to the testing location through the same connection.

The subject invention discloses a method for determining the amount of a target analyte in a fluid sample, comprising: a) providing a fluid sample; b) providing an assay device, the assay device comprising a test area that displays a measurable spatiotemporal pattern in response to an application of the fluid sample, the spatiotemporal pattern providing information related to the amount of target analyte present in the applied fluid sample and information related to the flow dynamics of the assay device; c) providing an imaging instrument operatively connected to the assay device, wherein the imaging instrument is capable of collecting and recording the spatiotemporal pattern as a set of numerical spatiotemporal data points; d) providing a computing device, operatively connected to the imaging instrument, wherein the computing device comprises an executable software program capable of analyzing the set of numerical spatiotemporal data points from the imaging instrument so as to calculate the amount of target analyte present in the fluid sample; e) applying the fluid sample to the assay device so as to induce the spatiotemporal pattern on the assay device; f) collecting a sufficient number of spatiotemporal data points from the spatiotemporal pattern of step e) on the imaging instrument to provide the set of numerical spatiotemporal data points for analysis; and g) analyzing the set of numerical spatiotemporal data points with the software program so as to determine the amount of target analyte in the fluid sample.

Another embodiment of the subject invention discloses a method for determining the amount of a target analyte in a fluid sample, comprising: a) providing a fluid sample; b) providing a plurality of fluid calibrator samples containing the target analyte at defined levels; c) providing a plurality of assay devices, each assay device comprising a test area that displays a measurable spatiotemporal pattern in response to an application of the fluid sample, the spatiotemporal pattern providing information related to the amount of target analyte present in the applied fluid sample and information related to the flow dynamics of the assay device; d) providing an imaging instrument operatively connected to the plurality of assay devices, wherein the imaging instrument is capable of collecting and recording the spatiotemporal pattern as a set of numerical spatiotemporal data points; e) providing a computing device operatively connected to the imaging instrument, wherein the computing device comprises an executable software program capable of analyzing the set of numerical spatiotemporal data points from the imaging instrument so as to calculate the amount of target analyte present in the fluid sample; f) applying one of the calibrators from the plurality of calibrators to one of the assay devices from the plurality of assay devices so as to induce the spatiotemporal pattern on the assay device; g) collecting a sufficient number of spatiotemporal data points from the spatiotemporal pattern of step f) on the imaging instrument to provide the set of numerical spatiotemporal data points for analysis; h) repeating steps f) and g) to create a plurality of sets of numerical spatiotemporal data points for the calibrator; i) repeating steps f)-h) for each calibrator from the plurality of calibrators to create a plurality of sets of numerical spatiotemporal data points for each calibrator from the plurality of calibrators; j) using the software program to create a database of the plurality of sets of numerical spatiotemporal data points generated for each calibrator from the plurality of calibrators; k) repeating steps f-j for the fluid sample; and l) analyzing the plurality of sets of numerical spatiotemporal data points from step k with the software program and the database so as to determine the amount of the target analyte in the fluid sample.

A further embodiment of the subject invention discloses a system for determining the amount of a target analyte in a fluid sample, comprising: a) a fluid sample; b) a plurality of fluid calibrator samples containing the target analyte at defined levels; c) an assay device, the assay device comprising a test area that displays a measurable spatiotemporal pattern in response to an application of the fluid sample, the spatiotemporal pattern providing information related to the amount of target analyte present in the applied fluid sample (and information related to the flow dynamics of the assay device; d) an imaging instrument operatively connected to the assay device, wherein the imaging instrument is capable of collecting and recording the spatiotemporal pattern as a set of numerical spatiotemporal data points; and e) a computing device operatively connected to the imaging instrument, wherein the computing device comprises an executable software program capable of analyzing the set of numerical spatiotemporal data points from the imaging instrument so as to calculate the amount of target analyte present in the fluid sample, the software program further comprising a database that contains a second set of numerical spatiotemporal data points derived from the set of fluid calibrator samples in step b), and a plurality of machine learning algorithms that use the second set of numerical spatiotemporal data points as training examples to establish calculations relating the second set of numerical spatiotemporal data points to the amount of target analyte present in a fluid sample.

In further embodiments of the subject invention, the spatiotemporal pattern results from a flow reaction operating in conjunction with at least one additional reaction selected from a group including, but not limited to, a biological reaction, a chemical reaction, biochemical reaction, an enzymatic reaction, and a binding reaction.

In additional embodiments of the subject invention, the assay device is an immunochromatographic assay device comprising a sample application region, a particle region containing reagent-coated test particles, and a test area containing a reagent-coated capture zone.

In even further embodiments of the subject invention, the information related to the amount of target analyte present in the applied fluid sample is derived from a binding of reagent-coated test particles in a reagent-coated capture zone of an immunochromatographic assay device.

In embodiments of the subject invention, the information related to the flow dynamics of the assay device is derived from measurable flow parameters related to a movement of reagent-coated test particles in a test area of an immunochromatographic assay device including, but not limited to, a parameter defining the amount of reagent-coated test particles that move from a particle region to the test area, a parameter defining the time required for the reagent-coated test particles to move from the particle region to a capture zone, a parameter defining the time required for the reagent-coated test particles to traverse the capture zone, a parameter defining the total amount of reagent-coated test particles that traverse the capture zone at a first defined time point, and a parameter defining the instantaneous concentration of reagent-coated test particles in the capture zone, or subsections of the capture zone, at defined time points.

In further embodiments of the subject invention the software program comprises a database that contains a second set of numerical spatiotemporal data points derived from a set of calibrator samples containing known levels of the target analyte, and a plurality of machine learning algorithms that use the second set of numerical spatiotemporal data points as training examples to establish calculations relating the second set of numerical spatiotemporal data points to the amount of target analyte present in a fluid sample.

In even further embodiments of the subject invention, the imaging instrument comprises a digital camera that records the set of numerical spatiotemporal data points as a set of gray scale values derived from a succession of digital images of the test area captured over time.

In further embodiments of the subject invention, the flow reaction is a capillary flow reaction.

In additional embodiments of the subject invention, the assay device is an immunochromatographic assay device.

In even further embodiments of the subject invention, the program analyzes the analyte information in the context of the flow information to determine the amount of target analyte present in the fluid sample.

In other embodiments of the subject invention, the calculations apply to an immunochromatographic assay device and involve establishing a relationship between the analyte information and the flow information in such a way as to define the respective contribution of target analyte and flow parameters to the amount of bound test particles in a capture zone, from which the amount of target analyte in a fluid sample may be determined.

In additional embodiments of the subject invention, the sample application region, particle region and test area are comprised of material selected from a group including, but not limited to, nitrocellulose, glass fiber, cellulose fiber, synthetic membranes and synthetic fibers.

In even further embodiments of the subject invention, the immunochromatographic assay device contains an absorbent pad in contact with the test area, the pad comprised of material selected from a group including, but not limited to, nitrocellulose, glass fiber, cellulose fiber, synthetic membranes and synthetic fibers.

In further embodiments of the subject invention, the reagent-coated test particles are produced from material selected from a group including, but not limited to, colloidal gold, polymer latex particles, colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; and liposomes.

In additional embodiments of the subject invention, the reagent-coated capture zone is coated with a member of a binding pair including, but not limited to, an antibody/antigen binding pair.

In further embodiments of the subject invention, the reagent-coated test particles are coated with a member of a binding pair including, but not limited to, an antibody/antigen binding pair.

In other embodiments of the subject invention, the assay device is a test strip maintained on a rigid backing.

In further embodiments of the subject invention, the assay device is a test strip maintained within a housing, the housing containing an opening to allow for sample application onto the sample application region and an opening to allow for observing the test area.

In even further embodiments of the subject invention, the target analyte is selected from a group of analytes including, but not limited to, proteins, peptides, small molecules, polysaccharides, antibodies, nucleic acids, drugs, toxins, viruses, virus particles, portions of a cell wall, metabolites, biological markers, and chemical markers.

In additional embodiments of the subject invention, the fluid sample is selected from a group including, but not limited to, whole blood, serum, plasma, urine, oral fluid, sweat, cerebrospinal fluid, milk, tissue extract, cellular extract, plant extract, growth media, petroleum products, and pharmaceutical products.

In further embodiments of the subject invention, the digital camera contains an image sensor selected from a group including, but not limited to, a CMOS image sensor and a CCD image sensor.

In other embodiments of the subject invention, wherein each spatiotemporal data point derives its spatial coordinate from its location on the digital image, the location corresponding to a location on the test area of the assay device.

In further embodiments of the subject invention, wherein each spatiotemporal data point derives its temporal coordinate from the time point at which the image containing the data point is captured.

In even further embodiments of the subject invention, the gray scale value of each spatiotemporal data point corresponds to an amount of reagent-coated test particles contained at the defined spatiotemporal coordinates of the data point.

In additional embodiments of the subject invention, the imaging instrument contains a light source selected from a group including, but not limited to, an LED light source, a fluorescent light source, an incandescent light source and a solar light source.

In further embodiments of the subject invention, the imaging instrument and the computer communicate through a physical connection.

In even further embodiments of the subject invention, the imaging instrument and the computer communicate through a wireless connection.

In other embodiments of the subject invention, the imaging instrument and the computer are two separate entities.

In further embodiments of the subject invention, the imaging instrument and the computer are combined into a single entity.

BRIEF DESCRIPTION OF THE DRAWINGS

Advantages of the present invention will be apparent from the following detailed description of exemplary embodiments thereof, which description should be considered in conjunction with the accompanying drawings:

FIG. 10A is a perspective view of an assay device being inserted into a spatiotemporal data recorder (designed according to FIG. 9A) indicating the manner in which the insertion process initiates the image capture process.

FIG. 10B is a perspective view of an assay device being inserted into a spatiotemporal data recorder (designed according to FIG. 9A) indicating the manner in which the insertion process initiates the image capture process.

FIG. 10C is a perspective view of an assay device being inserted into a spatiotemporal data recorder (designed according to FIG. 9A) indicating the manner in which the insertion process initiates the image capture process.

FIG. 11A is a perspective view of an assay device being inserted into a spatiotemporal data recorder (designed according to FIG. 9B) indicating the manner in which the insertion process initiates the image capture process.

FIG. 11B is a perspective view of an assay device being inserted into a spatiotemporal data recorder (designed according to FIG. 9B) indicating the manner in which the insertion process initiates the image capture process.

FIG. 11C is a perspective view of an assay device being inserted into a spatiotemporal data recorder (designed according to FIG. 9B) indicating the manner in which the insertion process initiates the image capture process.

FIG. 12A is a perspective view of an assay device being inserted into a spatiotemporal data recorder (designed according to FIG. 9C) indicating the manner in which the insertion process initiates the image capture process.

FIG. 12B is a perspective view of an assay device being inserted into a spatiotemporal data recorder (designed according to FIG. 9C) indicating the manner in which the insertion process initiates the image capture process.

FIG. 12C is a perspective view of an assay device being inserted into a spatiotemporal data recorder (designed according to FIG. 9C) indicating the manner in which the insertion process initiates the image capture process.

FIG. 12D is a perspective view of an assay device being inserted into a spatiotemporal data recorder (designed according to FIG. 9C) indicating the manner in which the insertion process initiates the image capture process.

FIG. 16A illustrates a data processing step wherein grids of cells are superimposed over digital images of test areas.

FIG. 16B illustrates a data processing step wherein grids of cells are superimposed over digital images of test areas.

FIG. 16C illustrates a data processing step wherein grids of cells are superimposed over digital images of test areas.

FIG. 16D illustrates a data processing step wherein grids of cells are superimposed over digital images of test areas.

FIG. 17A illustrates a data processing step wherein a digital image of a test area is converted to a grid of grayscale signals.

FIG. 17B illustrates the data processing step wherein a digital image of a test area is converted to a grid of grayscale signals.

FIG. 18A illustrates a data processing step wherein a grid of grayscale signals is converted to a grid of delta grayscale signals by calculating the difference between two designated images.

FIG. 18B illustrates the data processing step wherein a grid of grayscale signals is converted to a grid of delta grayscale signals by calculating the difference between two designated images.

FIG. 18C illustrates the data processing step wherein a grid of grayscale signals is converted to a grid of delta grayscale signals by calculating the difference between two designated images.

FIG. 19 illustrates a data processing step wherein the cells in each subzone of a grid are added up to create a single cell in each subzone.

FIG. 20 illustrates a data processing step wherein a grid of delta grayscale values is separated by channel to create multiple tables, each having a single cell in each subzone.

FIG. 21 illustrates a data processing step wherein a grid of delta grayscale values is first separated by channel, then certain channels are grouped and added up to create a single channel in each subzone.

FIG. 22 shows partial views of four spatiotemporal tables generated through the processing steps described in FIGS. 15-20.

FIG. 23 is an example of a spatiotemporal table comprised of 16 columns (subzones) and 48 rows (images).

FIG. 26 is a diagrammatic representation of a graph similar to the one shown in FIG. 24B along with a legend describing spatiotemporal datapoints and assay parameters as depicted in the graph.

FIG. 27A shows digital images of portions of the test areas for two strips (I and II) with differing concentrations of particles in the particle area, and outlines subzones 5 and 6 of the test areas FIG. 27B is a bar graph plotting the capture zone (subzone 5) signals for strips I and II shown in FIG. 27A.

FIG. 27C is a bar graph comparing the signal in subzone 6 as a function of image number for strips I and II.

FIG. 27D is a table comparing signal values for strips I and II, derived from FIGS. 27B and 27C.

FIG. 28A is a table of input data from an unknown sample.

FIG. 28B is a stored calibration curve used for calculating the value of the unknown sample that generated the input data given in FIG. 28A FIG. 28C shows the slope and Y-intercept values selected from the calibration curve shown in FIG. 28B (based in the signal provided in FIG. 28A), and also shows the calculation used to derive the output result.

FIG. 31A is a bar graph plotting signal in the capture and post-capture zones at single time point for strip I.

FIG. 31B is a bar graph plotting signal in the capture and post-capture zones at single time point for strip II.

FIG. 31C is a table comparing signal values for strips I and II, derived from FIGS. 31A and 31B.

FIG. 32A is a table of input data from an unknown sample.

FIG. 32B is a stored calibration curve used for calculating the value of the unknown sample that generated the input data given in FIG. 32A FIG. 32C shows the slope and Y-intercept values selected from the calibration curve shown in FIG. 32B (based in the signal provided in FIG. 32A), and also shows the calculation used to derive the output result.

FIG. 39A is a graph representing data from a sample reaction to be analyzed.

FIG. 39B is a graph showing flow curve data from the input sample reaction data.

FIG. 39C is a graph showing bind curves calculated from the flow curve data from FIG. 39B.

FIG. 39D is a calibration curve derived from the calculated bind curves shown in FIG. 39C.

FIG. 39E depicts an analysis of the sample bind curve using the calculated calibration curve

DETAILED DESCRIPTION OF THE INVENTION

Figure 1A:
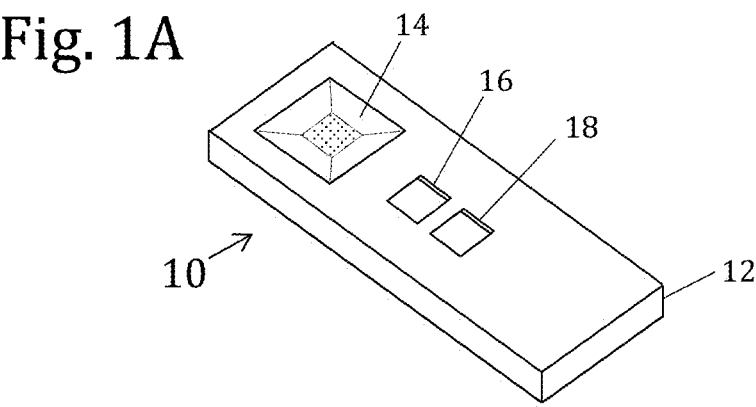
FIG. 1A is a perspective view of a prior art immunochromatographic assay device.
Figure 1B:
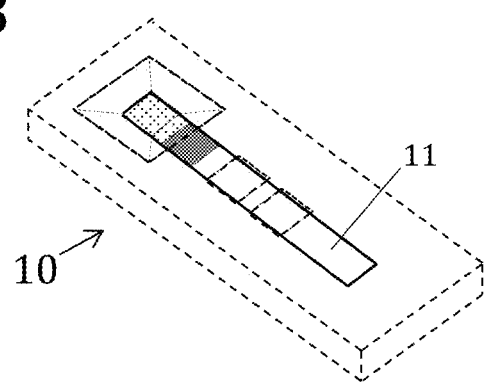
FIG. 1B is a partially phantom view of the FIG. 1A embodiment revealing a test strip predominantly concealed inside the device housing.
Figure 1C:
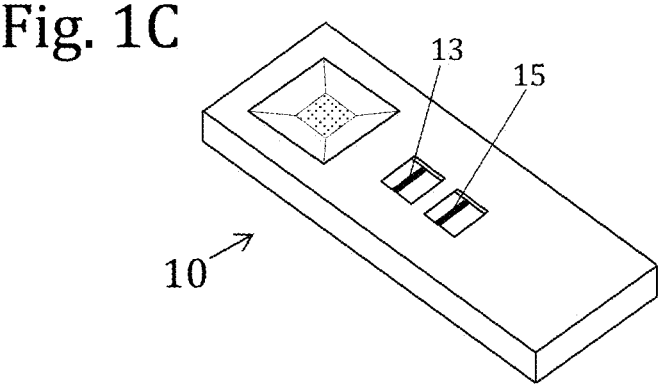
FIG. 1C is a view of the FIG. 1A embodiment showing formed test and control lines.

The following will describe, in detail, several embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

The current invention relates to methods of reliably and quantitatively determining the amount of an analyte of interest in a fluid sample using a flow-induced assay, such as an immunochromatographic assay, in which spatiotemporal measurements are recorded during the course of the assay reaction and subsequently analyzed. The invention also relates to devices comprised of flow-induced assays configured for spatiotemporal analysis, instruments for recording spatiotemporal datasets (spatiotemporal data recorders), and analysis programs for analyzing spatiotemporal datasets. In a preferred embodiment, the spatiotemporal data recorder incorporates a digital camera and the analysis program is performed on a computer with a software program.

The term, "analyte," as used herein, refers to a molecule or compound for which an amount will be measured. Examples of analytes include proteins, such as hormones or enzymes; glycoproteins; peptides; small molecules; polysaccharides; antibodies; nucleic acids; drugs; toxins; viruses or virus particles; portions of a cell wall; and other compounds. The analyte is in a "sample fluid". The sample fluid can be a fluid having relatively few components, for example, an aqueous solution containing the analyte of interest; alternatively, the sample fluid can be a fluid having many components, such as a complex biological fluid (e.g., whole blood, plasma, serum, urine, cerebrospinal fluid, or other biological fluid).

The term "assay," as used herein, refers to an in vitro procedure for analysis of a sample to determine the presence, absence, or quantity of one or more analytes. The term "reagent", refers to a physical component (existing in a solid, liquid, or gaseous state) used to carry out an assay, either alone or in combination with other components. Reagents may be comprised of elements, compounds, mixtures, chemicals, proteins, lipids, nucleic acids or solutions. The term "immunoassay", as used herein, refers to an assay that incorporates an antibody, antigen, or other binding component, as a reagent in the procedure.

A "flow-induced assay", as used herein, refers to a type of assay in which the reaction is initiated and/or propagated by a flowing action resulting from the application of a fluid, such as a sample fluid, to a reagent-containing device. The flowing action is typically generated by some form of capillary action that occurs when the fluid contacts suitable material in the device. The flowing action can induce the assay reaction by solubilizing, suspending and/or mobilizing assay reagents. Alternately, the flowing action can induce the assay reaction by transporting sample from a non-reactive application site to reagent-containing reaction site.

As used herein, an "immunochromatographic assay" is a type of flow-induced assay, and also a type of immunoassay, in which a fluid test sample containing analyte is contacted with a membrane having imbedded within it test particles coated with an analyte-specific reagent, such as antibodies to the analyte, causing capillary action of components of the system through the membrane, with a result indicated by detection of interaction between the test particles and the analyte in a reagent-containing capture zone of the membrane, the amount of test particles in the capture zone being related to the amount of analyte in the test sample. The term "immunochromatographic assay device", as used herein, refers to the apparatus on which the immunochromatographic assay procedure is carried out.

The term "spatiotemporal data point", as used herein, refers to a data point, such as a numerical value related to a signal in an assay, having both spatial (location in space) and temporal (location in time) associations. Multiple spatiotemporal data points comprise a "spatiotemporal dataset". A "spatiotemporal measurement" refers to a measurement in which one or more spatiotemporal data points are collected. Spatiotemporal datasets can be conveniently represented in a "spatiotemporal table" where the spatial association is organized into columns and the temporal association is organized into rows (or vice versa).

In one embodiment of the invention, an immunochromatographic assay is performed while undergoing spatiotemporal measurements. In such an immunochromatographic assay, a solid phase is used. The solid phase includes a membrane strip having an application region, a particle region, and a test area (alternately referred to as a test zone), with the test area being further sub-divided into a pre-capture zone, a capture zone and a post-capture zone. The membrane strip can be made of a substance having the following characteristics: sufficient porosity to allow capillary action of fluid along its surface and through its interior; the ability to allow movement of coated particles by capillary action (i.e., it must not block the particles); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the particle region of the strip is made of glass fiber, and the pre-capture, capture, and post-capture zones are made of a single piece of cellulose nitrate.

The "application region" is the position on the assay strip where a fluid sample is applied. The "particle region" of the membrane is adjacent to the application region. Imbedded in the particle region of the membrane is a population of "test particles" which are coated with analyte binding reagent, such as antibodies (or other types of molecules that specifically bind) to the analyte of interest. Alternately, such as in the case of certain competitive immunoassay formats, test particles may be coated with the analyte of interest or analogs of the analyte of interest. The population of particles varies, depending on the size and composition of the particles, the composition of the membrane, and the level of sensitivity of the assay. The population typically ranges approximately between $1 \times 10^3$ and $1 \times 10^9$ particles, although fewer or more can be used if desired. The test particles are particles which can be coated with analyte binding reagents (such as antibodies), analyte analogs (such as small molecule analyte conjugates) or the analyte of interest. Examples of particles include colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles. In a preferred embodiment, the particles are colloidal gold particles. In another preferred embodiment, the particles are polystyrene latex beads, and particularly, polystyrene latex beads that have been prepared in the absence of surfactant. The size of the particles is related to porosity of the membrane: the particles must be sufficiently small to be transported along the membrane by capillary action of fluid. The particles can be labelled to facilitate detection. Examples of labels include luminescent labels; colorimetric labels, such as dyes; fluorescent labels; or chemical labels.

In some embodiments, the particles and/or capture zone are coated with a reagent that specifically binds to the analyte of interest. In a preferred embodiment, the particles and/or capture zone are coated with antibodies to the analyte of interest. The antibodies can be monoclonal antibodies or polyclonal antibodies. The term "antibody", as used herein, also refers to antibody fragments which are sufficient to bind to the analyte of interest. Alternatively, molecules which specifically bind to the analyte of interest, such as engineered proteins having analyte binding sites, can also be used (Holliger, P. and H. R. Hoogenbloom, Trends in Biotechnology 13:7-9 (1995); Chamow, S. M. and A. Ashkenazi, Trends in Biotechnology 14:52-60:1996)). In another embodiment, if the analyte of interest is a ligand, a receptor which binds to the ligand can be used. If the analyte is an antibody of known specificity, the particles can be coated with the antigen against which the analyte-antibody is directed. In still another embodiment, if the analyte is a small molecule, such as a small molecule drug or toxin, a hapten or other small molecule conjugate may be used as the reagent.

The "capture zone" refers to an area on the membrane strip in which a "capture reagent" is immobilized. In one embodiment, the capture reagent is an analyte binding reagent, such as antibody directed against the same epitope of the analyte, or against a different epitope of the analyte, as antibodies coated onto the particles. Alternatively, the capture reagent can be the analyte of interest itself or an analog of the analyte, such as in the case of a competition assay. In still another embodiment, the capture reagent can be an antigen to an antibody analyte. The "pre-capture zone" refers to an area on the membrane strip between the particle region and the capture zone. The "post-capture zone" refers to the entire area on the membrane strip downstream of the capture zone, i.e. next to the capture zone on the side opposite the pre-capture zone. In some embodiments, the post-capture zone may contain an absorbent pad overlapping the membrane.

To perform the immunochromatographic assay, a sample fluid suspected of containing the analyte of interest is obtained. The fluid can be a fluid that wets the membrane material; that supports a reaction between the analyte of interest and the analyte binding reagent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution, such as a bodily fluid.

In a first embodiment of an immunochromatographic assay device, incorporating a sandwich assay format, the application region of the device is contacted with the fluid sample to be assayed for the analyte of interest. After the device is contacted with the fluid sample containing the analyte of interest at the application region, the device is maintained under conditions which allow fluid to transport the analyte by capillary action to the particle region of the device. When the analyte is transported to the particle region, analyte that is present in the fluid (if any is present) binds to the test particles imbedded in the particle zone. "Binding" of analyte to the test particles indicates that the analyte binding reagent coated onto the particle is bound to analyte of interest. A test particle which is "insufficiently bound" is one at which the binding sites of the analyte binding reagents coated onto the particle are not completely filled by the analyte of interest, such that binding reagent on the particle is capable of binding to additional analyte. A test particle which is insufficiently bound to analyte of interest, as described herein, can be bound to some analyte, or to no analyte. If no further analyte can be bound to the test particle, the analyte binding reagent-coated particle is said to be "saturated" with analyte. Test particles which have been maintained under conditions allowing analyte in the fluid to bind to the test particles imbedded in the particle zone are referred to herein as "contacted test particles". Contacted test particles may or may not have analyte bound to the analyte binding reagent, depending on whether or not analyte is present in the fluid sample and whether analyte has bound to the analyte binding reagent on the test particles. Thus, the population of contacted test particles may comprise particles having analyte bound to the analyte binding agent, as well as particles having no analyte bound to the analyte binding agent (just as the test particles initially have no analyte bound to the analyte binding agent).

Capillary action of the fluid from the fluid sample mobilizes the contacted test particles, and moves the contacted test particles along the device, first through a pre-capture zone, then into a capture zone on the device. The movement of contacted test particles can be arrested by binding to the capture reagent. The capture reagent binds to contacted test particles by binding to analyte which is bound to analyte binding reagent on the contacted test particles. The term, "capture-reagent-particle complexes", as used herein, refers to a complex of the capture reagent and contacted test particles. The capture-reagent-particle complexes are arrested (e.g., immobilized) in the capture zone, with the number of complexes being directly proportional to the amount of analyte in the sample fluid. Different labels are used as described above. Test particles that are not arrested in the capture zone continue to move through the capture zone and into the post-capture zone. Movement of the test particles through the post-capture zone continues as long as capillary action continues drawing fluid along the membrane strip.

In a second embodiment of an immunochromatographic assay device, incorporating a competition assay format, the application region of the device is contacted with the fluid sample to be assayed for the analyte of interest. After the membrane strip is contacted with the fluid sample containing the analyte of interest at the application region, the device is maintained under conditions which allow fluid to transport the analyte by capillary action to the particle zone of the device. When the analyte is transported to the particle zone, analyte that is present in the fluid (if any is present) binds to the test particles imbedded in the particle zone. "Binding" of analyte to the test particles indicates that the analyte binding reagent coated onto the particle is bound to analyte of interest. A test particle which is "insufficiently bound" is one at which the binding sites of the analyte binding agents coated onto the particle are not completely filled by the analyte of interest, such that binding reagent on the particle is capable of binding to additional analyte. A test particle which is insufficiently bound to analyte of interest, as described herein, can be bound to some analyte, or to no analyte. If no further analyte can be bound to the test particle, the analyte binding reagent-coated particle is said to be "saturated" with analyte. Test particles which have been maintained under conditions allowing analyte in the fluid to bind to the test particles imbedded in the particle zone are referred to herein as "contacted test particles". Contacted test particles may or may not have analyte bound to the analyte binding reagent, depending on whether or not analyte is present in the fluid sample and whether analyte has bound to the analyte binding agent on the test particles. Thus, the population of contacted test particles may comprise particles having analyte bound to the analyte binding agent, as well as particles having no analyte bound to the analyte binding agent (just as the test particles initially have no analyte bound to the analyte binding agent).

Capillary action of the fluid from the fluid sample mobilizes the contacted test particles, and moves the contacted test particles along the membrane, first through a pre-capture zone, then into a capture zone on the membrane. The movement of contacted test particles can be arrested by binding to the capture reagent, comprised of immobilized analyte or analyte analog. The capture reagent binds to contacted test particles by binding to analyte binding reagent not bound to sample analyte. The capture-reagent-particle complexes are arrested (e.g., immobilized) in the capture zone, with the number of complexes being inversely proportional to the amount of analyte in the sample fluid. Different labels are used as described above. Test particles that are not arrested in the capture zone continue to move through the capture zone and into the post-capture zone. Movement of the test particles through the post-capture zone continues as long as capillary action continues drawing fluid along the membrane strip. In a third embodiment of an immunochromatographic assay device, incorporating an alternate competition assay format, analyte-binding reagent is coated in the capture zone, while analyte, or analyte analog, is coated on the test particles.

The invention further involves subjecting the immunochromatographic assay device to spatiotemporal measurements during the course of the assay reaction. Spatiotemporal measurements are recorded with a spatiotemporal data recorder. In a preferred embodiment, the recorder contains a digital camera. The camera captures digital images with an image sensor, such as a charge coupled device (CCD) or complementary metal oxide semiconductor (CMOS), each comprising an array of photo sites (also referred to as photo sensors, photo detectors, pixel sensors, or pixel sites). Assay signals are generated in the form of photons (from a light source) reflecting off the test area and into a photosite within the image sensor, with the number of photons entering a specific photosite being proportional to the number of particles in a defined location of the test zone at the time the image is captured. Photons entering a photosite are converted to a proportional number of electrons, which are then measured and assigned a numerical value known as a "grayscale" value. The grayscale value is finally mapped to a location on a two-dimensional grid (based on the location of the photosite within the image sensor), which ultimately defines the captured image. Thus, the test area is converted to a grid of numerical values, wherein each value can be mapped to a precise location on the test zone, and is proportional to the number of test particles at that location.

In a preferred embodiment, the image sensor contains sufficient photo sites to produce a minimum of 300,000 grayscale values per captured image. In another preferred embodiment, each photosite is able to capture multiple grayscale levels, such as in the case of image sensors that are Fovean sensors. Furthermore, the recorder is programmable to capture multiple images over time. In a preferred embodiment, the recorder captures digital images at a minimum rate of one frame per second. In another preferred embodiment, the recorder captures digital images at a minimum rate of one frame per 5 seconds. In still another preferred embodiment, the recorder captures digital images at a minimum rate of one frame per 15 seconds. As the recorder captures images, each photosite in the image sensor is able to collect signals indicative of the assay reaction. Broadly speaking, a "signal" is defined as the grayscale level recorded by a photosite, or the difference between two grayscale levels at different locations, indicating the presence of test particles or fluid sample in the area targeted by the photosite. Alternately, a signal can be defined as a change in the grayscale level (at the same location) recorded by a photosite from one image to the next, resulting from test particles and/or sample fluid moving into, or out of, the area targeted by the photosite. The magnitude of change in the signal is proportional to the number of test particles present in the area recorded by the photosite at a given time.

In a preferred embodiment of the methods, the immunochromatographic assay device is first positioned for data collection prior to sample application. Positioning of the device is such that the recorder is able to capture images that incorporate the entire test zone, including the pre-capture zone, capture zone, and post-capture zone. Following the positioning of the device, the recorder begins collecting images at a programmed rate. As the recorder captures images, sample fluid is applied to the application region of the device. The recorder continues collecting images for sufficient time until the assay reaction is completed. In one embodiment, the completion time is determined by a threshold signal occurring in one or more areas of the image. For example, the assay may be deemed to have been completed once signal (resulting from the presence of test particles) is detected in a specific area of the post-capture zone. Alternately, the assay may be deemed completed at a specified time interval (such as five minutes) that commences when signal is first detected in the pre-capture zone.

Completion of the recording process results in the generation of a series of digitally captured images encompassing the test zone of the immunochromatographic assay device, over the course of an assay reaction, induced by the application of sample fluid. Each image is comprised of a two-dimensional grid of picture elements or "pixels", and each pixel contains at least one grayscale value. More broadly stated, each image is derived from a dataset of grayscale values, with each grayscale value having an associated spatial value. Collectively, the captured images can be used to create a spatiotemporal dataset representing the entire assay reaction. The dataset can be represented as a set of data points, with each data point containing information relating to three values; 1) a "spatial value" representing the discrete location of the data point in the two-dimensional grid comprising the captured image 2) a "temporal value" representing the time in which the image, and hence data point, was captured, and 3) a "signal value" representing the grayscale level of the data point. If a photosite generates a single grayscale value, the total number of data points in a given dataset can be calculated by multiplying the number of images captured with the number of pixels comprising the test zone (pre-capture zone, capture zone, and post-capture zone). For example, if a recorder captures 300 images of the test zone, with each test zone image comprised of 50,000 pixels, the total number of data points in the dataset would be 300×50,000 or 15,000,000 data points. Note that if a photosite generates multiple grayscale values (per capture), the total number of data points is further multiplied by the number of grayscale values per photosite. In other embodiments, the digital camera incorporates a color filter, such as a Bayer filter, in which each grayscale value is generated through one of a set of color filters (e.g. red, green and blue filters). In such cases, the data point may incorporate a fourth value identifying the color filter through which the grayscale value was generated. It should also be noted that with certain digital color camera formats, multiple color values may be defined for a given location on the image, but some of those values may be calculated rather than directly measured.

In a preferred embodiment of the spatiotemporal data recorder, the digital camera is contained within a housing element. The housing element incorporates an opening suitable for the insertion of the assay device. The opening further comprises a device holder accommodating the assay device. Insertion of the assay device into the holder results in the proper orientation and distance of the device test zone with respect to the lens of the digital camera, allowing for optimal image capture of the test zone. The recorder also may contain a light source, such as an LED light, situated within the housing element in a manner as to provide optimal lighting conditions for the image capture process. In one embodiment, the digital camera is stationary within the housing. In another embodiment, the digital camera is mobile within the housing. Both the digital camera and the light source may be operated by a controller, also situated within the housing element. In one embodiment, the controller may be connected to an ON/OFF switch accessible outside of the housing element. In another embodiment, the ON/OFF switch may be situated within the housing element and triggered by the insertion of the assay device. In another embodiment, the camera and light source are controlled by a computer connected directly to the camera and light source (through, for example, USB connection) or wirelessly (through, for example, a Bluetooth connection). The image capturing process may be controlled by the ON/OFF switch. Alternately, the recorder may be ON, but residing in a stand-by mode, with the image capture being triggered non-mechanically, such as by the presence of a bar code within the image.

Analysis of the spatiotemporal dataset recorded by the spatiotemporal data recorder may occur within the recorder itself, or on a separate instrument connected to the recorder. In a preferred embodiment, the analysis is performed on a separate computer connected to the reader, such as through a USB or wireless connection. The computer contains a software program designed to receive the spatiotemporal dataset and perform a series of analyses, which may incorporate, without limitation, mathematical formulas, tables, standard curves, algorithms and empirically defined values, coefficients, constants, and the like, both general and specific to the assay being analyzed. Generally speaking, the spatiotemporal dataset represents a "spatiotemporal pattern", and the software program is designed for "spatiotemporal pattern analysis".

In a preferred embodiment, the software program uses spatiotemporal datasets established from previously performed assays that incorporate fluid samples of known analyte concentration, such as calibrator or standard samples (a calibration database). In other embodiments, analysis of the spatiotemporal dataset may occur partially or entirely on one or more computers, or other analyzers, situated in locations separate from the site in which the assay is performed. In such cases, datasets and results may be transported between instruments by way of a telecommunication connection, such as an internet connection.

The calibration dataset can be used to define relationships between signals measured in the capture zone (resulting from both flow dynamics and analyte concentration) and signals in the pre-capture zone and post-capture zone (resulting from flow dynamics only). By creating multiple spatiotemporal datasets for a given calibrator, statistically significant ranges of relationships can be established between signals in the various zones, allowing for analyses that incorporate, without limitation, statistically significant interpolations, extrapolations, and threshold settings. The system also allows for synchronized comparisons that "weight" the various signals. For example, the analysis may be weighted to compare different datasets at a time point wherein a specific number of test particles have migrated into the post-capture zone. In still another application, the calibration dataset may be used to establish quality control thresholds, such as establishing a minimum and maximum time allowance for test particles to migrate from the particle zone to the capture zone, determined from signals measured in the pre-capture zone.

In a preferred embodiment, the spatiotemporal dataset is organized into a spatiotemporal table, wherein the spatial component of the data is identifiable by column position and the temporal component of the table is identifiable by row position (or vice versa). The spatial component can be defined as a series of subzones in the test area, with each subzone associated with one of the three primary zones (pre-capture zone, capture zone, or post-capture zone). Signals taken from the subzones that encompass the capture zone can be used to determine a "binding signal", which is a value either directly or indirectly proportional to the concentration of analyte in the test sample (depending on whether the test is a sandwich assay or a competitive assay, respectively). Signals taken from the subzones of the pre-capture and post-capture zones can be used to determine "assay parameters", which are measured and/or calculated values that reflect the movement of the particles in the test area and are directly or indirectly proportional to a binding signal in a manner that is independent of analyte concentration. By determining one or more parameters that are associated with a given binding signal, it is possible to provide a precise context of the assay conditions that generated the binding signal. In a preferred embodiment, the relationship between binding signals and assay parameters is established through a computational method of classification, such as through the use of machine learning. Machine learning is a branch of artificial intelligence concerning the construction and study of systems that can learn from data. The core of machine learning deals with representation and generalization. Representation of data instances and functions evaluated on these instances are part of all machine learning systems. Generalization is the property that the system will perform well on unseen data instances. Generalization in this context is the ability of an algorithm to perform accurately on new, unseen examples after having trained on a learning data set. The core objective of a learner is to generalize from its experience. The training examples come from some generally unknown probability distribution and the learner has to extract from them something more general, something about that distribution that allows it to produce useful predictions in new cases.

Machine learning algorithms can be organized into a taxonomy based on the desired outcome of the algorithm or the type of input available during training the machine. "Supervised learning" algorithms are trained on "labeled" examples, i.e., input where the desired output is known. The supervised learning algorithm attempts to generalize a function or mapping from inputs to outputs which can then be used to speculatively generate an output for previously unseen inputs. In a preferred embodiment, a program incorporating supervised machine learning algorithms is used, wherein fluid samples of known analyte concentration, such as calibrator or standard samples, are provided as labeled examples upon which the system can be trained. Other types of machine learning algorithms that may be employed include "unsupervised", "semi-supervised", "transduction" and "reinforcement learning" algorithms.

While the embodiments described herein have focused on the use of immunochromatographic assay devices, it should be understood that the invention is broadly applicable to other flow-induced assay devices, such as chemistry and enzymatic assay devices. For example, a flow-induced assay strip designed to measure the levels of an analyte in a biological sample matrix (such as glucose in serum) may contain chemical or enzymatic reagents impregnated onto a membrane which generate an observable (chemical or enzymatic) spatiotemporal color pattern upon exposure to the sample. This pattern may be defined by analyte-dependent observations (such as a color signal on the membrane that darkens in relation to analyte concentration) and analyte-independent observations (such as non-uniform coloration across the membrane due to variable fluid flow patterns). This analyte-independent variability, a potential source of erroneous result interpretations, could be addressed using spatiotemporal pattern analyses incorporated in the current invention.

In the following descriptions of the drawings, like reference numbers are used to identify like elements. Furthermore, certain drawings are meant to illustrate major features of exemplary embodiments in a diagrammatic manner. The diagrams are not intended to depict every feature of actual embodiments nor relative dimensions of the depicted elements, and are not drawn to scale.

Figure 2:
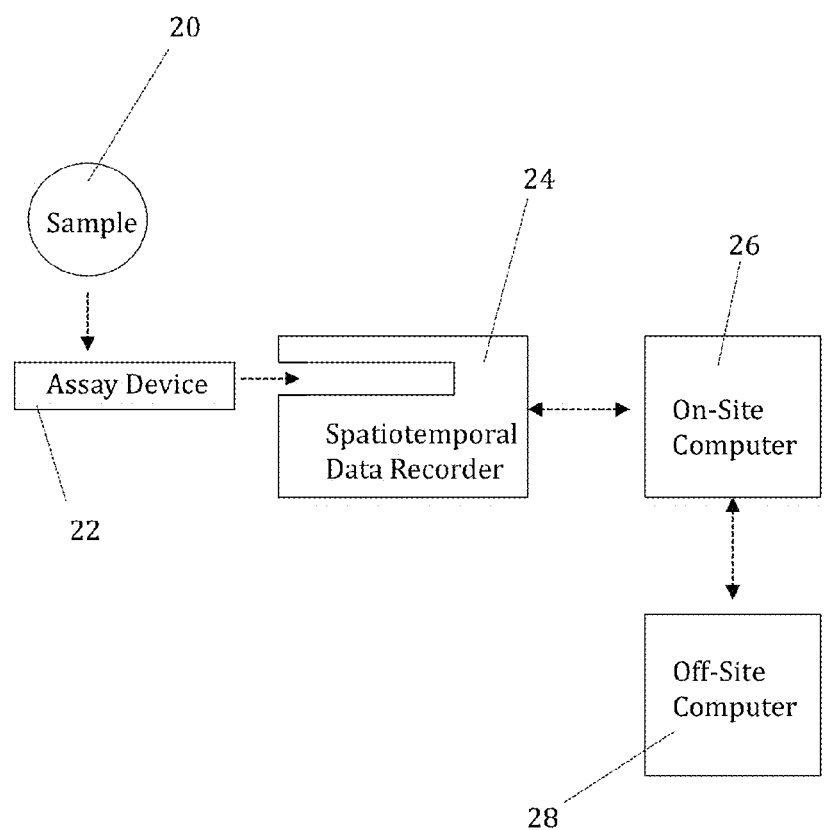
FIG. 2 shows the components of a spatiotemporal analysis system incorporating a fluid sample, an assay device, a spatiotemporal recorder an on-site computer and an off-site computer.

FIG. 2 shows a diagrammatic embodiment of the interacting components within the system. Fluid sample 20 is applied to the assay device 22, thereby initiating a measurable flow-induced assay reaction. The assay device is inserted into the spatiotemporal data recorder 24 allowing the recorder to record the assay reaction as a series of digital images. This image data is collected by the linked on-site computer 26 and analytically processed. The computer may perform all of the processing steps or work in conjunction with an off-site computer 28 such as a server linked to the on-site computer by way of an internet connection. In a preferred embodiment, the assay device is inserted into the recorder, and image recording is initiated, before sample is applied to the device. In FIG. 2 the recorder and on-site computer are illustrated as separate components. In some embodiments the recorder and computer may constitute a single component. For example, a suitably housed and application fitted smartphone (containing a digital camera, light source and computer) may serve the function of both the spatiotemporal data recorder and computer.

Figure 3:
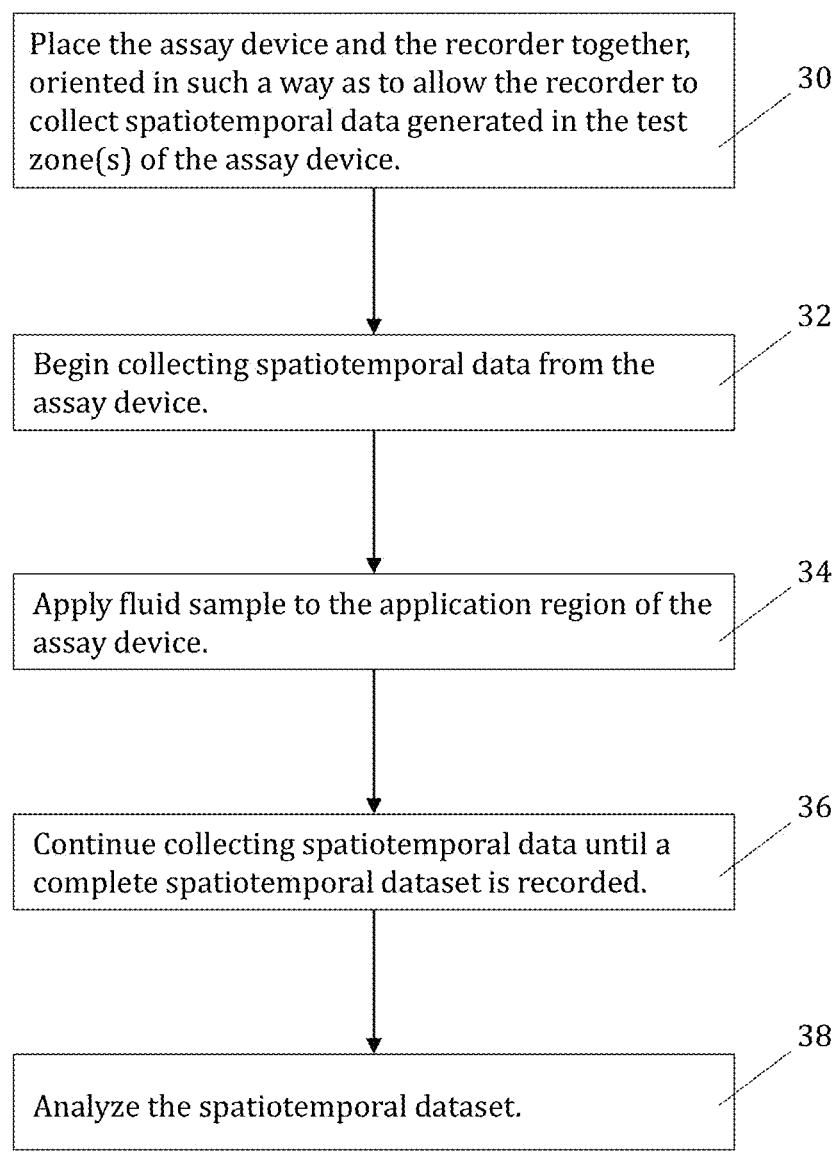
FIG. 3 is a flow diagram of an embodiment of a method of analyzing a fluid sample using a spatiotemporal analysis system.

FIG. 3 shows a flow diagram of an embodiment of a method of analyzing a fluid sample using the system components described in FIG. 2. More specifically, the diagram describes the order of steps taken in a preferred embodiment of a method of the invention. In the first step of the method 30, the assay device and recorder are brought together appropriately in preparation for image capture. In the second step 32, the recorder begins capturing images of the test zone. It is important to note that the recorder can actively capture images of the test area before any assay reaction has occurred on the assay device. In this manner the invention is able to record the precise moment at which fluid sample makes initial contact with the test area membrane (the effective start time of the reaction) without having to rely on the user to actively define the start time, thus avoiding the potential for human error and the need for training. While the recorder is actively collecting images, the sample is applied as described in 34. Following application of fluid sample, the recorder continues collecting data until a defined completion point is reached 36, and the resulting spatiotemporal dataset is analyzed 38. In other embodiments, the assay device may be designed to provide a time delay between the time when sample is applied to the device and the time when the assay reaction occurs. In such an embodiment the delay time would allow the user to apply sample to the device prior to insertion of the device into the recorder.

Figure 4:
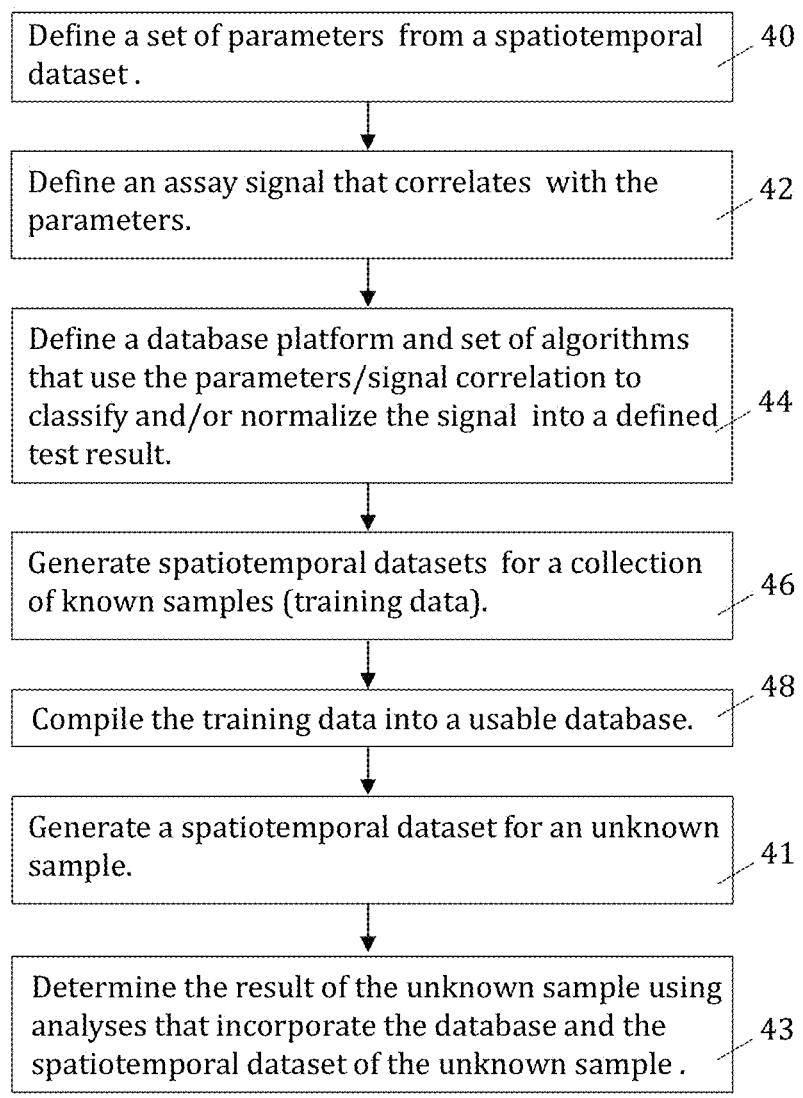
FIG. 4 is a flow diagram of a preferred embodiment of FIG. 3 step 38.

A number of strategies may be employed for the analysis step in 38. FIG. 4 shows a flow diagram of a preferred embodiment. In the first step, a set of parameters is defined from the spatiotemporal dataset 40, followed by a step defining an assay signal that correlates with these parameters 42 (in other embodiments, step 42 may occur before step 40, or the two steps may occur simultaneously). A database platform is then constructed along with a set of operations designed to receive and process the parameters/signal data, 44. With the database platform established, a collection of spatiotemporal datasets are then generated and stored (in the database) from assay reactions performed on known samples (containing known quantities of analyte) 46. After a sufficient number of datasets from known samples have been generated and stored, the system is prepared to analyze unknown samples. Thus an unknown sample is run 41, and the resulting spatiotemporal dataset is analyzed using the database 43. In a preferred embodiment, the analysis incorporates machine learning algorithms.

Figure 5:
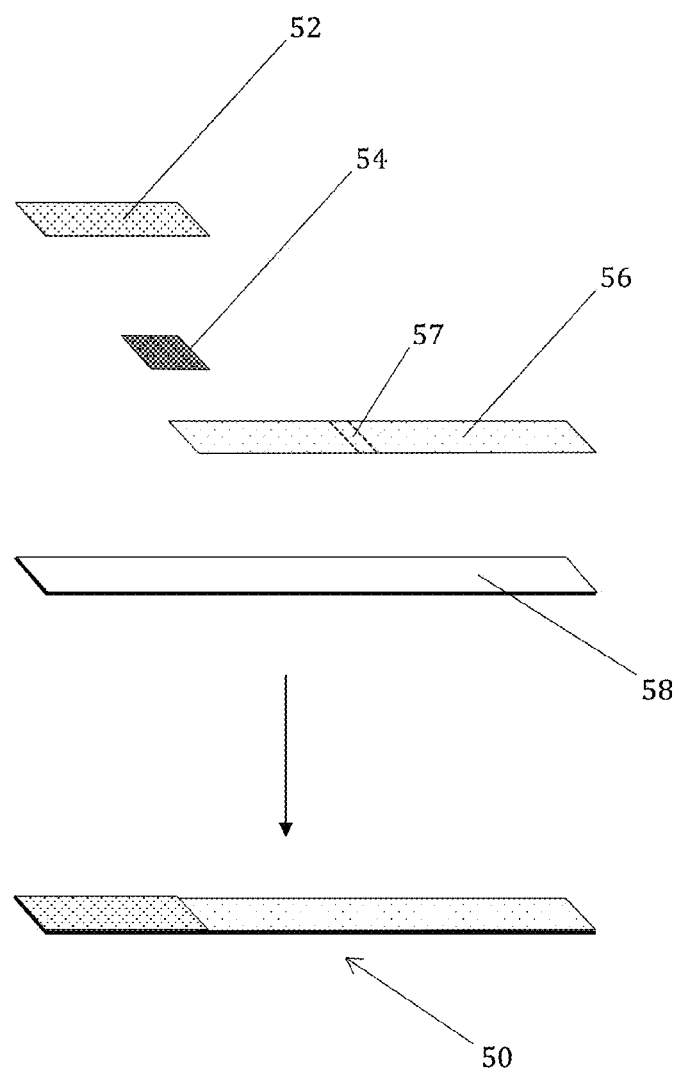
FIG. 5 is an exploded view of a typical immunochromatographic strip.

In a preferred embodiment, the assay device incorporates an immunochromatographic assay strip. FIG. 5 shows a perspective view of a typical immunochromatographic assay strip 50, along with an exploded view of the strip. The strip contains overlaid porous membranes (52, 54 and 56) supported by a non-porous back support, 58. The first membrane 52 is incorporated in the sample application region of the assay device and receives fluid sample. This membrane overlays a second membrane 54 that contains reversibly imbedded test particles, represented in the drawing by the dark coloration of the membrane. The test particle containing membrane contacts a third membrane 56 that contains a band of irreversibly coated reagent, non-visible in its unreacted state but identified in FIG. 5 as the area between two dotted lines 57. The membranes are supported by the non-porous back support 58. This support may be opaque if the assay reaction is viewed from the top side of the strip, or transparent if the assay reaction is viewed from the bottom side of the strip.

Figure 6:
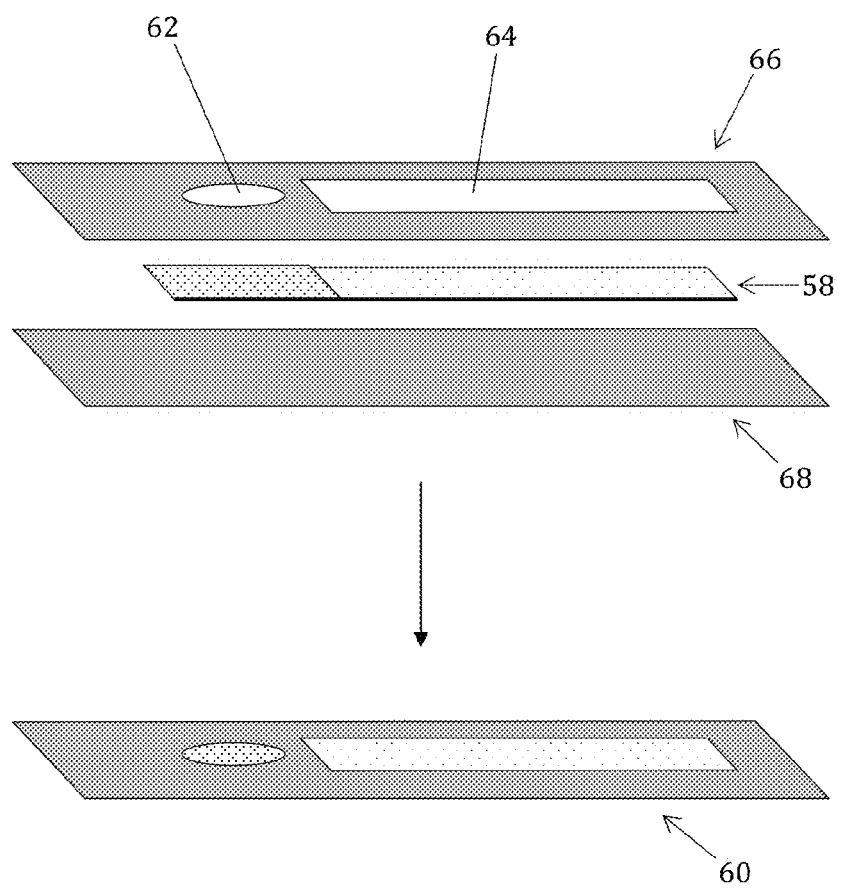
FIG. 6 is an exploded view of an embodiment of an assay device incorporating a housing designed for horizontal insertion and top-down imaging in a spatiotemporal data recorder.
Figure 7:
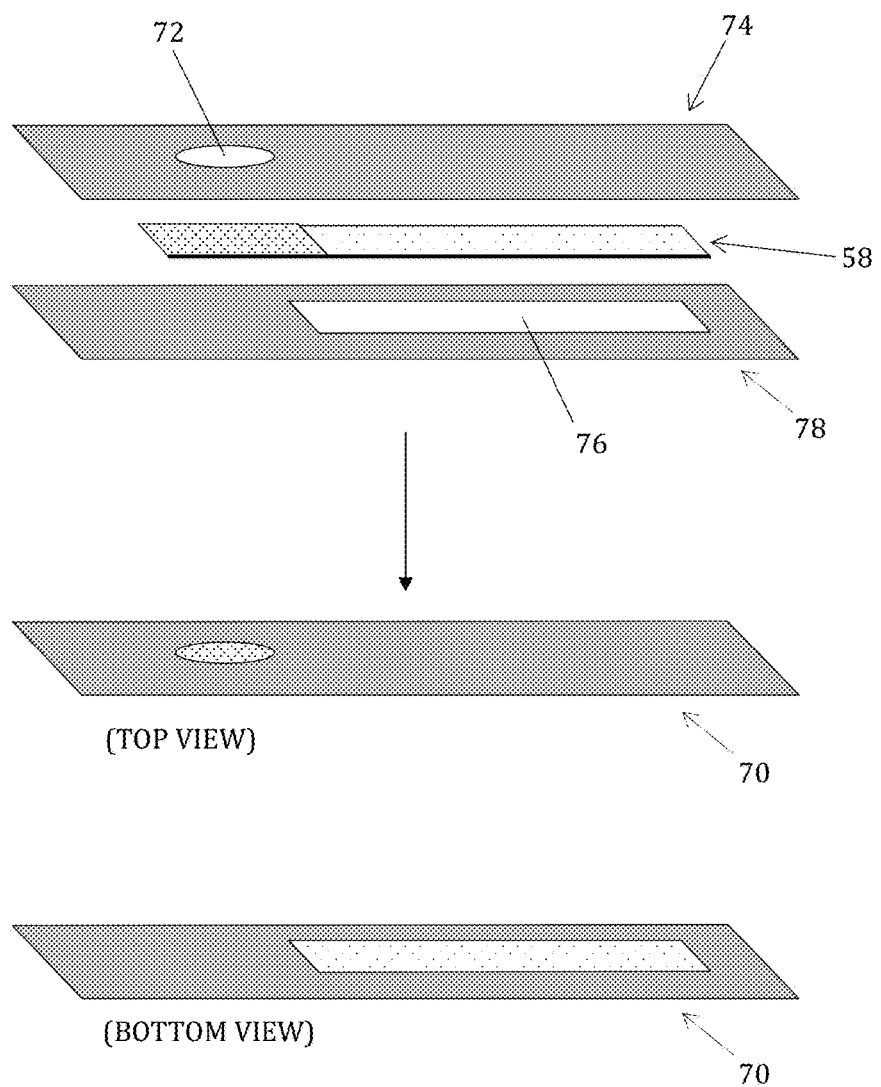
FIG. 7 is an exploded view of an embodiment of an assay device incorporating a housing designed for horizontal insertion and bottom-up imaging in a spatiotemporal data recorder.

In a preferred embodiment, the immunochromatographic assay strip is contained in a housing that allows for both sample application and analysis of the test area. The housing may be configured in one of several ways depending on the orientation of the assay device with respect to the spatiotemporal recorder. FIG. 6 depicts a configuration that accommodates both the sample application site and the test area on the same side of the assay device. The strip 58 is placed between a top component 66 and a bottom component 68 of the housing which come together to enclose the strip and form the assay device 60. The top component contains two openings: one for the sample application site 62 and one for the test area 64. FIG. 7 depicts a configuration that accommodates the sample application site on the top side and the test area on the bottom side of the assay device. The strip 58 is placed between a top component 74 and a bottom component 78 of the housing which come together to enclose the strip and form the assay device 70. The top component contains an opening 72 for the sample application site while the bottom component contains an opening 76 for viewing the test area. The top and bottom housing components depicted in FIGS. 6 and 7 may be joined together by a number of approaches. One approach is to incorporate interlocking edges around the perimeters of the components. When joined together, these edges would create a side dimension to the device imparting a certain degree of thickness to the device and creating a cavity within the device where the strip is housed. Such a design may also accompany the inclusion of a well that defines the opening for the sample application site. Within the cavity, the housing may include a design feature that contacts the strip in the parts of the strip where membranes are overlaid so as to ensure suitable contact between the membranes.

Figure 8:
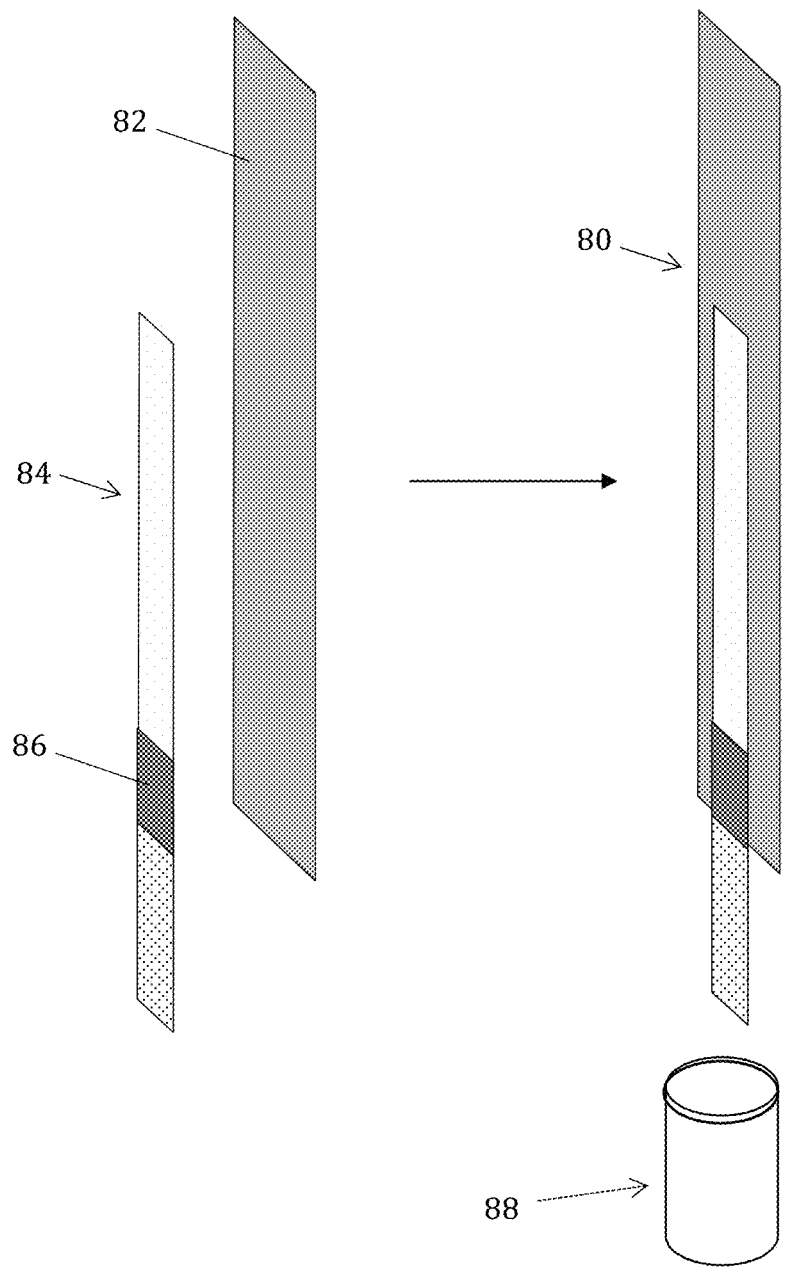
FIG. 8 is an exploded view of an embodiment of an assay device incorporating a housing designed for vertical insertion in a spatiotemporal data recorder.

The assay devices described in FIGS. 6 and 7 depict configurations that are designed to be placed horizontally into or onto a reader. In another preferred embodiment, the assay device is configured to be place vertically into a reader. FIG. 8 depicts one such configuration, where the strip 84 is attached to a housing 82. Rather than being placed directly onto the assay device, sample is placed into a vial 88 and the strip component of the device is dipped into the vial. In this configuration a label 86 may also be included on the strip in the parts of the strip where membranes are overlaid so as to ensure suitable contact between the membranes. The strip and housing may be joined together by a number of methods, such as by the use of an adhesive. In some embodiments, the strip and housing may be reversibly joined, allowing the housing to be re-used with multiple strips.

Figure 9A:
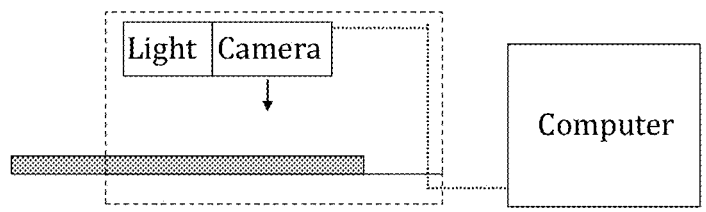
FIG. 9A is a diagrammatic side view of a spatiotemporal data recorder containing an inserted assay device (designed according to FIG. 6) and drawn in a partial phantom view to show the orientation of the camera and light source with respect to the assay device.
Figure 9B:
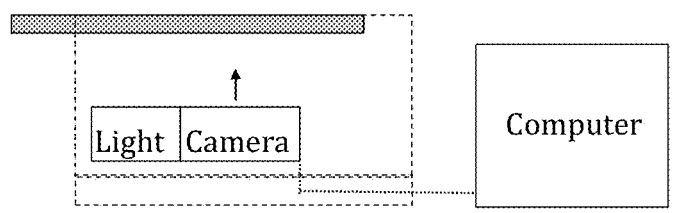
FIG. 9B is a diagrammatic side view of a spatiotemporal data recorder containing an inserted assay device (designed according to FIG. 7) and drawn in a partial phantom view to show the orientation of the camera and light source with respect to the assay device.
Figure 9C:
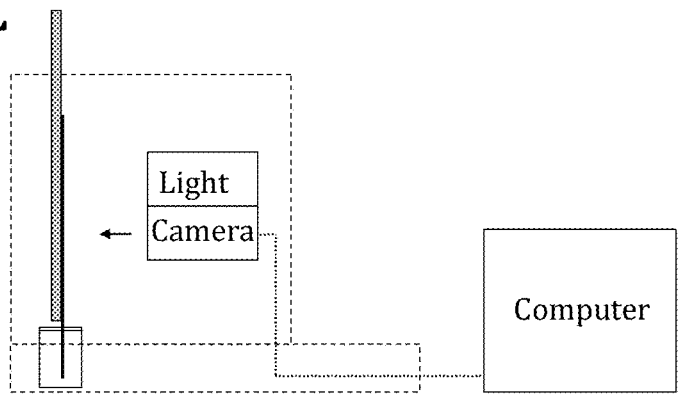
FIG. 9C is a diagrammatic side view of a spatiotemporal data recorder containing an inserted assay device (designed according to FIG. 8) and drawn in a partial phantom view to show the orientation of the camera and light source with respect to the assay device.

FIGS. 9A-9C are a set of diagrammatic representations depicting assay devices placed into spatiotemporal recorders, illustrated in such a way as to show the orientation of the device with respect to the camera and light source in the recorder. FIG. 9A depicts an assay device configured as shown in FIG. 6, where the test area is exposed on the top of the device and images are captured by a camera located above the device. FIG. 9B depicts an assay device configured as shown in FIG. 7, where the test area is exposed on the bottom of the device and images are captured by a camera located below the device. FIG. 9C depicts an assay device configured as shown in FIG. 8, where the test area is exposed in a vertical orientation and images are captured by a camera located alongside the device.

In a preferred embodiment of the spatiotemporal recorder, the insertion of the assay device into the recorder triggers the instrument to begin capturing images. FIGS. 10A-10C illustrates this function with a strip 60 designed according to the configuration shown in FIG. 6. Prior to the insertion of the assay device into the recorder 100, the camera is in the "Off" state (FIG. 10A). Insertion of the device into a slot 102 engages the recorder to turn "On" and begin capturing images (FIG. 10B), which continues as sample is applied to the assay device (FIG. 10C). The Off/On switching of the recorder could occur through the use of a mechanical switch (which could also control the lighting) or through photo-optic detection such as by sensing a barcode. FIGS. 11A-11C represents the same function as FIGS. 10A-10C except that the assay device 70 is designed according to the configuration shown in FIG. 7. Rather than having a slot, the recorder 110 contains a sliding lid 112 that covers an opening and is displaced when the device is inserted as shown in FIG. 11B. Compared with the FIG. 10A-10C design, this design allows greater access to the sample application site for the addition of sample (FIG. 11C).

FIGS. 12A-12D illustrate an embodiment of the spatiotemporal recorder designed to accommodate assay devices configured as shown in FIG. 8. The recorder contains a vial holder 126 where a sample vial 88 is positioned and sample is applied, as shown in FIG. 12A. After sample is applied, a chamber 124 placed over the vial (FIG. 12B). A slot 122 on the top of the chamber lines up with the vial when appropriately placed, allowing the assay device 80 to be inserted in such a way as to cause the sample application portion of the strip to be submerged into the sample fluid containing vial (FIGS. 12C and 12D). Insertion of the device into the slot engages the recorder to begin capturing images. Alternately, the recorder may be engaged by the movement of the chamber over the vial, through a mechanical connection.

Figure 14:
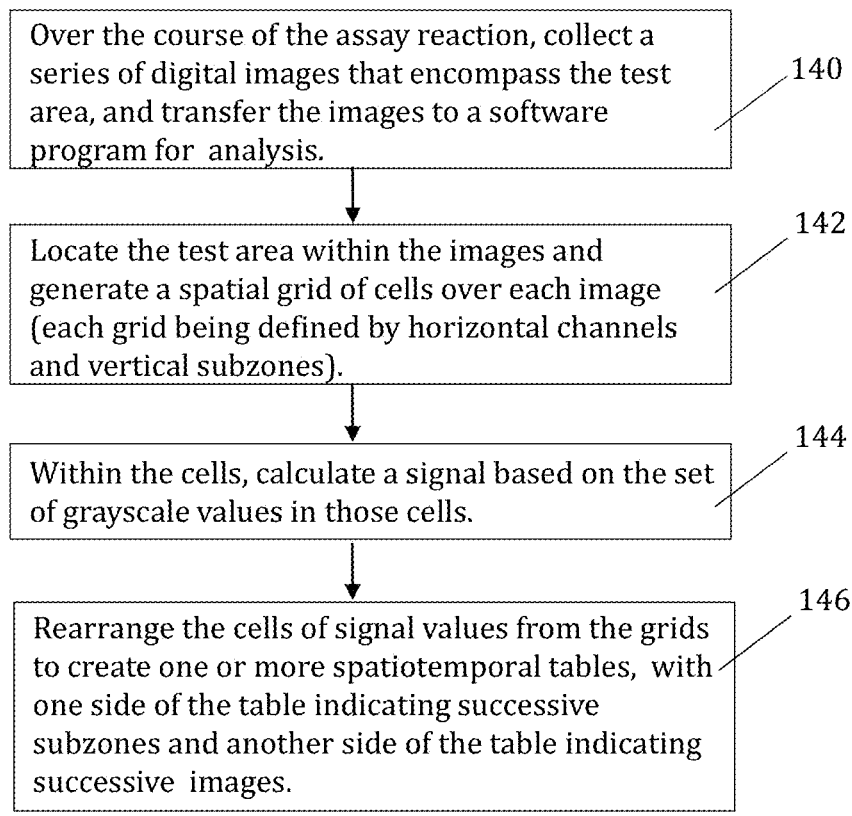
FIG. 14 is a flow diagram of an embodiment of a method for converting digital images into tables of spatiotemporal data.

The spatiotemporal data recorder is connected to a computer that receives the digital images from the recorder as input data and performs a series of analytical steps leading to a useful output result. These analytical steps are performed, at least in part, by a software program contained on the computer. In a preferred embodiment, the analytical steps performed by the software program include converting the input digital images into a table of numerical values called a spatiotemporal table. FIG. 14 is a flow diagram outlining the basic series of steps in this operation. First the images are collected and transferred to the software program 140. The program then locates the portion of the image that represents the test area and generates a spatial grid over this area on each image 142. The cells of the grid identify discrete regions of the image (at discrete points in time) that are associated with a set of grayscale values. These values are used to calculate a single numerical signal value 144. These signals are then organized according to their associated spatial and temporal values to create one or more spatiotemporal tables 146 that are used for analysis.

The present invention is illustrated by the following examples, which are not intended to be limiting in any way.

Example 1: Preparation of a Vertically Oriented Immunochromatographic Assay Device for the Measurement of Aflatoxin Analyte An immunochromatographic assay device was constructed based on the design described in FIG. 8. A housing component was made by cutting a rigid piece of cardboard into a rectangle and attaching an immunochromatographic strip to the housing with double stick tape. The immunochromatographic strip contained reagents for the detection of aflatoxin, and was prepared by standard methods well known in the field. Briefly, a solution of aflatoxin-BSA conjugate was striped onto a plastic backed nitrocellulose sheet to create a capture zone approximately 1 mm wide. Colloidal gold nanoparticles coated with monoclonal anti-aflatoxin antibody were dried onto a strip of glass fiber, which was then partially overlaid onto the nitrocellulose sheet to create a particle region and define a pre-capture zone (between the particle region and the capture zone). A portion of the strip was secured to the plastic backing with adhesive. A second strip of glass fiber was then partially overlaid onto the particle region to create a sample application region, with a portion of this strip secured to the plastic backing with adhesive. A strip of tape was placed over the particle region wide enough to encompass a portion of the sample application region and the pre-capture zone. This tape served to ensure the overlapping membranes were sufficiently contacting one another. On the other end of the sheet, a strip of absorbent material was partially overlaid onto the nitrocellulose membrane to function as an absorbent pad, with a portion of this material secured to the plastic backing with adhesive. Finally, the sheet was cut into strips, each strip having a width of 4 mm and a length of 9 cm.

Figure 13A:
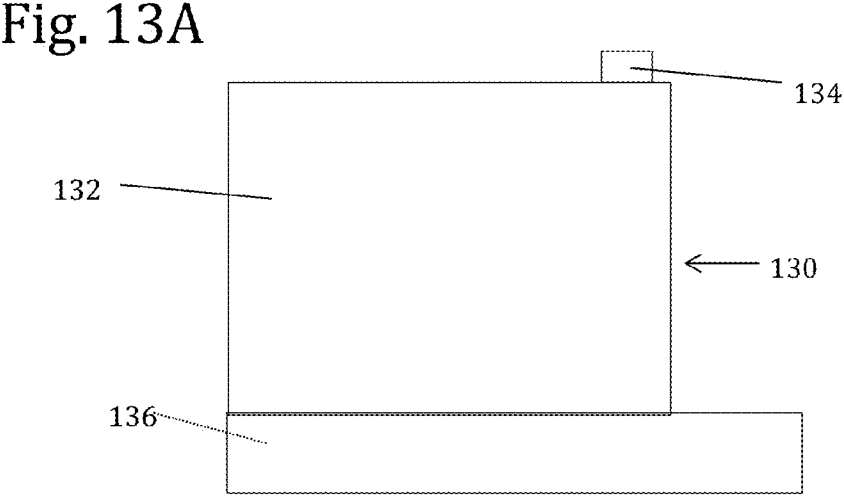
FIG. 13A is a diagrammatic side view of a spatiotemporal data recorder configured for a vertically inserted assay device.
Figure 13B:
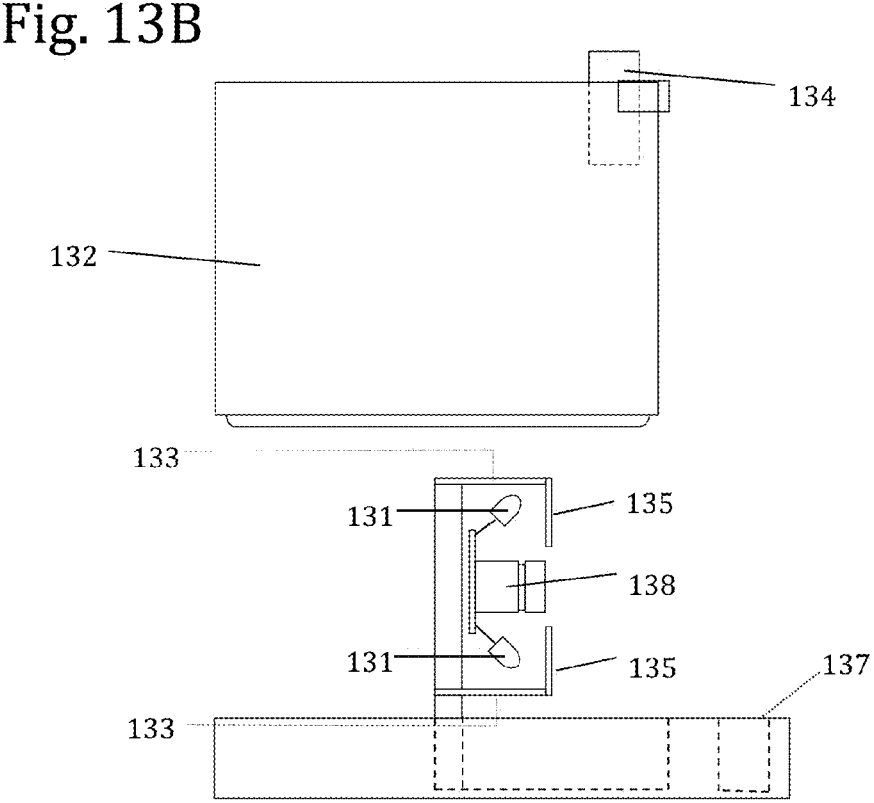
FIG. 13B is a diagrammatic side view of the FIG. 13A recorder with the chamber lifted to show the enclosed camera and light source.

Example 2: Construction of a Spatiotemporal Data Recorder Designed to Accommodate Vertically Oriented Assay Devices To analyze the assay devices prepared as described in Example 1, a spatiotemporal data recorder was constructed based on the design shown in FIGS. 12A-12D. FIGS. 13A-13B are a detailed diagrammatic side view of the recorder. As shown in FIG. 13A the recorder is comprised of a movable chamber 132 situated on top of a base 136. The chamber contains an assay device guide 134 for accepting a vertically inserted assay device. A digital camera and light source are contained inside the chamber. FIG. 13B shows the instrument with the chamber lifted so that the camera 138 and LED lights 131 are in view. The camera contains a 0.3 megapixel CMOS image sensor on a circuit board, with a lens over the sensor. The LED lights are attached to the circuit board in this embodiment allowing for both the camera and light source to be operated by (and draw power from) a single source. To homogenize the light source over the test area, opaque shields 135 are placed between the LED bulbs and the assay device, and diffuser film 133 is place above and below the bulbs. All components within the chamber (particularly the inner chamber wall) are colored white to further homogenize this light source. On the base of the recorder is a holder 137 for receiving the sample vial. After the sample-filled vial is in place, the chamber can be slid forward allowing for the device guide to line up with the vial. An opening in the front of the chamber allows the chamber to slide over the vial.

The camera is connected to an external computer via a USB cable. The computer contains a software program (developed in C# language as a part of Microsoft.NET Framework) designed to control the camera and LED lights, define a time interval for automatically capturing images (for example, 1 image per second), import the image data, store the image data, process the image data into a set of tables based on the grayscale values contained within the image data, and perform mathematical calculations on the numerical values within the tables. For the processing step, the program allows the user to first define a rectangular area within the first image captured (note that because the test area of the assay device is also rectangular, it is possible to select the entire test area). This area will then be assigned to all the images captured in a particular assay analysis. The user is then able to assign a grid of square cells over the rectangle (as described in Example 3) to generate the set of tables used for analysis.

Figure 15:
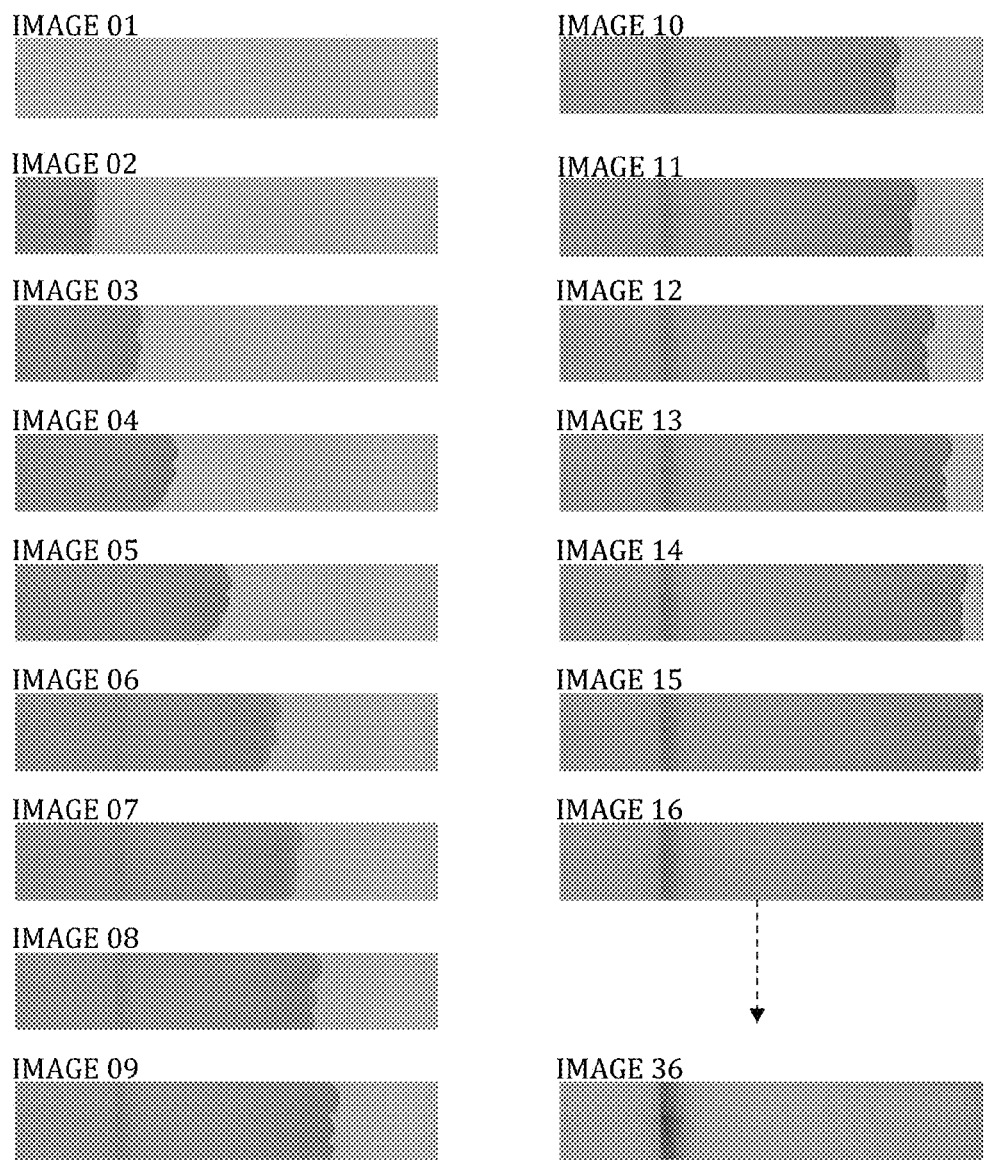
FIG. 15 shows a set of test areas collected as digital images from a spatiotemporal data recorder.

Example 3: Sequential Digital Images of an Assay Device Test Area Captured on a Spatiotemporal Data Recorder Using a vertical test system with components designed as shown in FIG. 8 and FIGS. 12A-12D, the spatiotemporal data recorder (described in Example 2) begins capturing images of the immunochromatographic assay device upon insertion of the device into the recorder, and sequential images are captured at defined time intervals over the course of the flow-induced assay reaction. FIG. 15 shows a set of captured images obtained from a recorder after insertion of an assay device containing a competitive immunoassay strip configured into an assay device as described in Example 1. The test area has the dimensions of approximately 4×18 mm and the recorder incorporates a 0.3 megapixel CMOS image sensor and 2 LED lights, oriented as shown in FIGS. 13A-13B. Images were captured at 5 second intervals, with Image 01 representing the first image captured, Image 02 representing the second image captured, etc. The sample tested was a known negative wheat extract prepared by combining 10 grams of wheat flour with 20 ml of an extract solution (25% ethanol and 75% water) and shaking vigorously for one minute. The sample was then allowed to settle and the extract was filtered through filter paper. One ml of extract was placed in a test vial which was then placed in the vial holder of the recorder. After sliding the chamber over the vial, the aflatoxin assay device was inserted through the device slot such that the application area of the test strip became submerged in the sample vial. Image capturing began immediately after the strip was inserted.

Image 01 shows the test area prior to the migration of the particle flow stream into the test area, at which point all of the particles are immobilized in the particle area. Image 02 shows the test area after flow-induction has occurred. At this point the particles have been hydrated by the sample and the particle/sample flow stream begins migration into the pre-capture zone of the test area, visually observable by the darker coloration on the left side of the image (the flow stream migrates from left to right in the figure because the images were rotated 90 degrees clockwise). At the time point captured by Image 03, the front of the flow stream has migrated through the capture zone and into the post-capture zone. As the flow stream continues migrating through the test area, the flow of particles through the capture zone results in particle binding within this zone, visible as a dark band about 5 mm from the left edge of the test area. The front of the flow stream can be tracked up until Image 16, at which point it migrates onto an absorbent pad. As the flow stream continues its migration onto the absorbent pad, particles continue to flow through the capture zone until a completion point is reached when particles are suitably bound within the capture zone and/or suitably depleted from the pre-capture and post-capture zones.

Example 4: Converting Each Digital Image of the Test Area into a Grid of Numerical Values After a set of digital image data is produced by the spatiotemporal data recorder, the set is received by a software program for analysis. In a preferred embodiment, the first principal step in this analysis is to convert each set of image data corresponding to the test area into a useful grid of numerical values derived from the gray scale numbers comprising the data. For descriptive purposes, FIGS. 16A-16D show an image of a test area taken from the dataset described in Example 1 (it should be understood that the image represents a collection of numerical grayscale numbers rendered into color pixels). A grid of square cells is superimposed over the image defining discrete spatial locations on the image. For optimal analysis, the software may define this grid with different size cells. Three different grids are shown in FIG. 16B-16D corresponding to arrangements of 3×15 cells (FIG. 16B), 6×30 cells (FIG. 16C) and 12×60 cells (FIG. 16D). Each cell represents a unique location in the test area identifiable in the figure by alphanumeric labeling (for example, the cell in the top left corner of each grid is defined as "A1"). More broadly, each grid is definable by a set of horizontal "channels" and vertical "zones".

Each cell in the grid encompasses three sets of grayscale values corresponding to the red, blue and green channels of the image sensor that recorded the digital images. In a preferred embodiment of the data analysis, each set of grayscale values is converted into a single value by calculating the average within the cell, resulting in each cell containing three "signals" defined by the average grayscale value in the cell. This process is illustrated in FIGS. 17A-17B. FIG. 17A shows a 3×15 grid superimposed over Image 3 of the assay reaction described previously. FIG. 17B shows a table of mean grayscale values generated from this grid based on data from the green channel. Similar grids are also created for data retrieved from the red and blue channels (not shown). It should be noted that each grayscale value may at this stage be deemed a "spatiotemporal data point" as the "signal" (the grayscale value) has an associated spatial value (the alphanumeric value indicating its location in the grid and, hence, the location in the test area that it measures) and a temporal value (the image number, indicating the time point in the course of the assay reaction that the data was collected).

In some cases (such as to correct for non-uniform lighting) it is useful to process the signal further into a "delta grayscale" value, such as by subtracting an image that contains no portion of the particle flow stream in the test area. FIGS. 18A-18C show an example of this processing step. FIG. 18A is the grayscale table generated from Image 03. FIG. 18B is the grayscale table generated from Image 01, wherein no portion of the particle flow stream was present in the test area. FIG. 18C is a delta grayscale table generated by subtracting the signal in each cell of image 01 from its corresponding cell in Image 03. For example, the signal in cell 1A of FIG. 18C (44) was calculated by subtracting the signal in cell 1A of FIG. 18B (208) from the signal in cell 1A of FIG. 18A (166). Note that after processing the grayscale tables into delta grayscale tables, the signal in each cell becomes directly proportional to the concentration of particles in the cell location at the time the image is captured.

Example 5: Creation of Spatiotemporal Tables

The delta grayscale tables created as shown in Example 2 can be further processed to create one or more spatiotemporal tables, which is a table of signals organized such that each signal is associated with a spatial value (such as a subzone number) and a temporal value (such as an image number). In one embodiment, each delta grayscale table is first reduced to a single row by adding up all of the cells in a given subzone as shown in FIG. 19. In another embodiment, the channels are separated to create multiple individual rows from each table as shown in FIG. 20. In still another embodiment, the channels are separated to create multiple individual rows, and then a subset of these rows are re-grouped and reduced to a single row by adding up all of the cells in a given zone as shown in FIG. 21, where channels A, B and C are separated then channels A and B are re-grouped and reduced to a single row.

Each row is then grouped by image number, resulting in a table of signals where the horizontal location in the table indicates the image number for a given signal and the vertical location in the table indicates the subzone number for a given signal. FIG. 22 represents four different spatiotemporal tables (partially shown) generated from the delta grayscale tables given in Example 2. The first table is comprised of signals created by adding up the three cells in each subzone. The next three tables are comprised of separated channels (with the channel identity indicated in the top left corner of the table).

A more complete spatiotemporal table is shown in FIG. 23. This table was generated from an assay device using a competitive immunochromatographic strip for the detection of aflatoxin. The sample tested was a known negative wheat extract prepared and assayed as described in Example 1. The signal values in the table were calculated from cells that captured an area of 1 mm2 on the test strip and the rows correspond to a single channel on the strip. Grayscale values were taken from the green channel of the digital camera and images were captured at a rate of 1 image/5 seconds. The capture zone is located entirely in subzone 5. Thus subzones 1-4 represent the pre-capture zone and subzones 6-16 represent the post-capture zone.

Example 6: Defining Binding Signals and Associated Parameters from Spatiotemporal Tables Signals taken from the area encompassing the capture zone are used to determine a "binding signal", which is a value either directly or indirectly proportional to the concentration of analyte in the test sample (depending on whether the test is a sandwich assay or a competitive assay, respectively). The binding signal may also be broadly referred to as "analyte information". Signals taken from the areas of the pre-capture and post-capture zones (which may also be broadly referred to as "flow information") are used to determine "assay parameters", which are measured and/or calculated values that reflect the presence and movement of the particles in the test area and are directly or indirectly proportional to a binding signal in a manner that is independent of analyte concentration. By determining one or more parameters that are associated with a given binding signal, it is possible to provide a precise context of the assay conditions that generated the binding signal, thereby allowing for a more accurate, precise and reliable calculation of assay results.

Figure 24A:
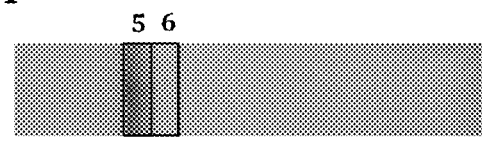
FIG. 24A is a digital image of a test area highlighting two subzones within the capture and post-capture zones.
Figure 24B:
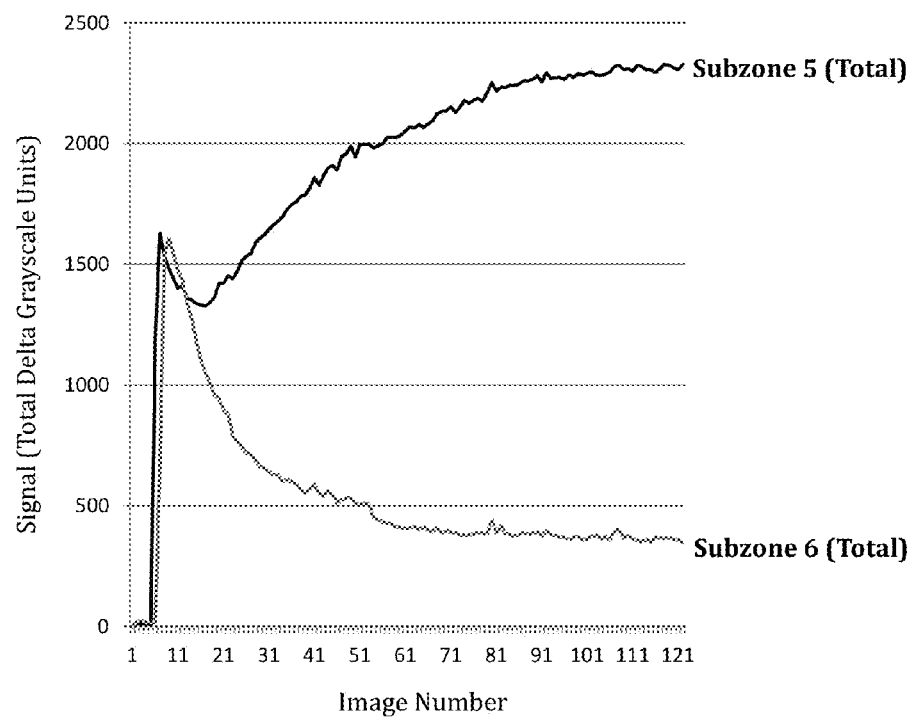
FIG. 24B is a graph plotting the signal development (as a function of image number) in the two subzones highlighted in FIG. 24A.

Sections of a spatiotemporal table can be represented in graph form to better illustrate the relationship and calculations employed between assay parameters and binding signals. FIG. 24A shows one of the digital images of an aflatoxin strip assayed with a negative grain extract as described in Example 1. A spatiotemporal table was generated from the analysis, comprised of 17 zones (4 cells per zone totaled up to define each signal) and 125 images. Zone 5 encompasses the capture zone and zone 6 encompasses an immediate area of the post-capture zone equal in size to the capture zone. FIG. 24B shows the signals in each zone graphed as a function of image number (thus representing the signal in each respective location on the strip at specific time intervals). The graph (which can be referred to as a spatiotemporal data graph) shows how the particle flow stream crossed both zones within the first minute of the assay reaction (note the early peak of around 1600 delta grayscale units for both lines). As the reaction proceeded over time, Zone 5 initially became reduced in signal (as the concentrated front of the flow stream passed through the zone) then consistently gained more signal (as particles bound in the capture zone) while Zone 6 became concomitantly reduced in signal (as particles flowed through unbound and were gradually exhausted from the particle region). For discussion purposes, the line on the spatiotemporal data graph depicting the capture zone may be referred to as the "bind curve" while the line depicting the zone outside the capture zone may be referred to as the "flow curve".

Figure 25A:
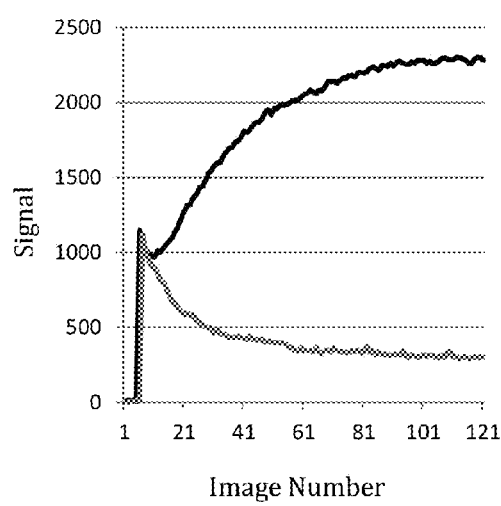
FIG. 25A is a graph plotting the signal development (as a function of image number) in the two subzones highlighted in FIG. 24A on an aflatoxin assay strip following application of a wheat extract containing 0 ng/ml aflatoxin.
Figure 25B:
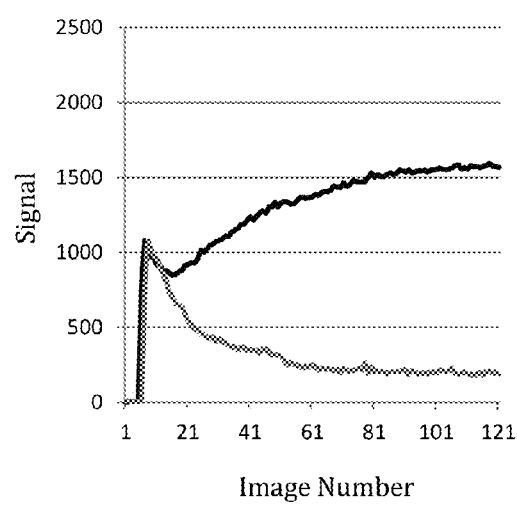
FIG. 25B is a graph plotting the signal development (as a function of image number) in the two subzones highlighted in FIG. 24A on an aflatoxin assay strip following application of a wheat extract containing 2.5 ng/ml aflatoxin.
Figure 25C:
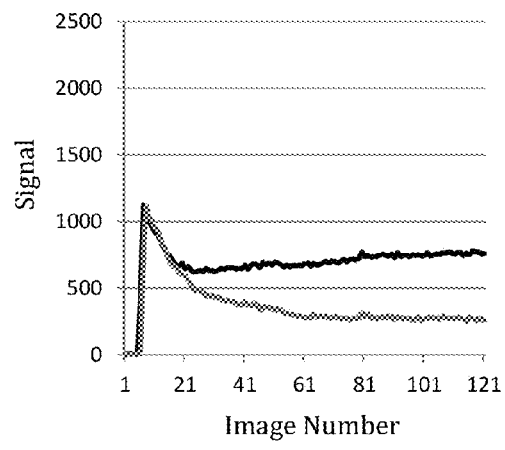
FIG. 25C is a graph plotting the signal development (as a function of image number) in the two subzones highlighted in FIG. 24A on an aflatoxin assay strip following application of a wheat extract containing 5 ng/ml aflatoxin.
Figure 25D:
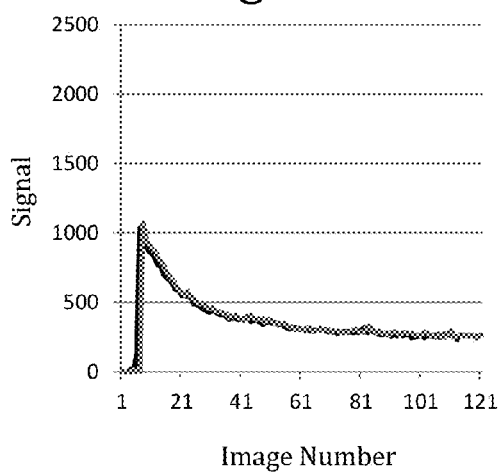
FIG. 25D is a graph plotting the signal development (as a function of image number) in the two subzones highlighted in FIG. 24A on an aflatoxin assay strip following application of a wheat extract containing 10 ng/ml aflatoxin.

To demonstrate the test system with positive aflatoxin samples, negative wheat extract (prepared as described in Example 3) was spiked with pure aflatoxin at concentrations ranging from 0-10 ng/ml, and each sample was then run on the system described in Example 3. FIGS. 25A-25D show the spatiotemporal data graphs for samples containing aflatoxin at 0 ng/ml (FIG. 25A), 2.5 ng/ml (FIG. 25B), 5 ng/ml (FIG. 25C) and 10 ng/ml (FIG. 25D).

FIG. 26 is a diagrammatic representation of the type of graph shown in FIGS. 24A-24B and 25A-25D. Several spatiotemporal data points (A through G) are identified on the graph in relation to the Zone 6 line, and one data point ($S_b$), which serves as the binding signal, is identified in relation to the Zone 5 line. One or more relevant properties of these data points is described below the graph under the heading "SPATIOTEMPORAL DATAPOINTS". The Zone 6 data points can be further processed to produce assay parameters. Examples of these parameters are shown in the list in FIG. 26. The common features of these parameters are that they are independent of the concentration of analyte in the sample and that they provide information that can be used to assist in the qualification or quantification of the associated $S_b$ signal (which is dependent on both flow stream dynamics and the concentration of analyte in the sample). For example, the parameter described as "incubation time" measures the period of time that elapses between the point when particles first enter the capture zone and the point when the $S_b$ signal is defined. For a sandwich assay this parameter value is directly proportional to the $S_b$ value (the greater the incubation time, the greater the signal).

Example 7: Correlating Binding Signals with Assay Parameters to Generate Results (Format 1)

An experiment was performed to demonstrate the manner in which information from an assay parameter could be used to improve the accuracy and reliability of an assay. Two different assay strips were prepared, such that one strip (II) contained half the amount of test particles coated in the particle region compared with the other strip (I). The strips were similar to those described in Example 1 (competitive immunochromatographic strips designed for the detection of aflatoxin). Both strips were run in a spatiotemporal data recorder designed similar to the instrument shown in FIGS. 13A-13B. Sequential digital images were collected as described in Example 1 (60 images at 5 second intervals), and spatiotemporal tables were created from these images as described in Examples 2 and 3. Negative wheat extract (prepared as described in Example 1) was used as the test sample.

FIG. 27A shows digital images of portions of the test areas for strips I and II, and outlines subzones 5 and 6 of the test areas (which are identical to those described in Example 4). Both strips show the assay reaction after 5 minutes. As the images clearly show, strip II contains significantly less particle binding in the capture zone compared with strip I, owing to the difference in initial particle concentrations. The signal in each capture zone (total delta grayscale in zone 5 minus total delta grayscale in zone 6) is plotted on a bar graph shown in FIG. 27B and indicates a reduction in binding signal of about 46% when comparing strip II to strip I. Taking strip I to be a "standard" or correctly functioning strip in this experiment, strip II would serve as a stand-in for a "faulty" strip (identical to a malfunctioning strip in which roughly half the particles fail to mobilize off the particle pad and migrate through the strip). Under conventional analysis, such a strip could likely be misinterpreted as a false positive, as conventional analysis is unable to distinguish variable flow dynamics with competitive binding inhibition from sample analyte.

FIG. 27C shows a set of bar graphs representing signal in zone 6 captured in successive images over the course of the assay reaction. Each bar in the graph is proportional to the "instantaneous" concentration of particles in zone 6 at a given time point. This data can be used to create an assay parameter defined as the sum of the bar values from the start of the reaction to the time point when the binding signal is measured. FIG. 27D is a table listing both the zone 5 signals (binding signal at the 5 minute time point) and the zone 6 signals (total cumulative sum of the signals at each time point) for each strip. The table also shows the ratio of the zone 5 and zone 6 results for each strip. Note that the ratio is 0.24 for both strips. This indicates that the spatiotemporal analysis of zone 6 allows for the determination of an assay parameter that could serve a normalizing function in the analysis of the capture zone. For example, a calibration curve could be generated (for a batch of strips produced in accordance with Strip I) that defines the signal as "zone 5 at 5 min.)/zone 6 (total: 0-5 min.)". The strips would thus be expected to produce a signal of "0.24" for a negative wheat extract even when the strips demonstrate highly variable rates of particle migration from the particle region.

FIGS. 28A-28C depict an example of an unknown sample analyzed using the normalized signal calculation described in FIGS. 27A-27D. FIG. 28A shows a table with spatiotemporal data used to calculate a signal value of 0.055 for the unknown sample. FIG. 28B shows a calibration table generated from known calibration samples and stored in the analysis program. With the input signal of 0.055, the program first selects the appropriate slope and Y-intercept values from the calibration curve. Because 0.055 falls between the mean signals from the 40 and 160 calibrators (0.084 and 0.036, respectively), the slope and Y-intercept values located in the row with the 40 calibrator are selected. These values are then used in conjunction with the unknown sample signal to derive a result, using the formula: RESULT=$10^{((y-b)/m)}$ where y is the unknown sample signal, m is the slope, and b is the Y-intercept. FIG. 28C shows the values incorporated into the equation, leading to an output result of 92.4

Note that in the above calculations of the parameter, each data point that was summed up from subzone 6 was given equal weighting. In other applications it may be beneficial to weight each data point differently, or divide the data points in such a way as to produce multiple parameters.

Figure 29A:
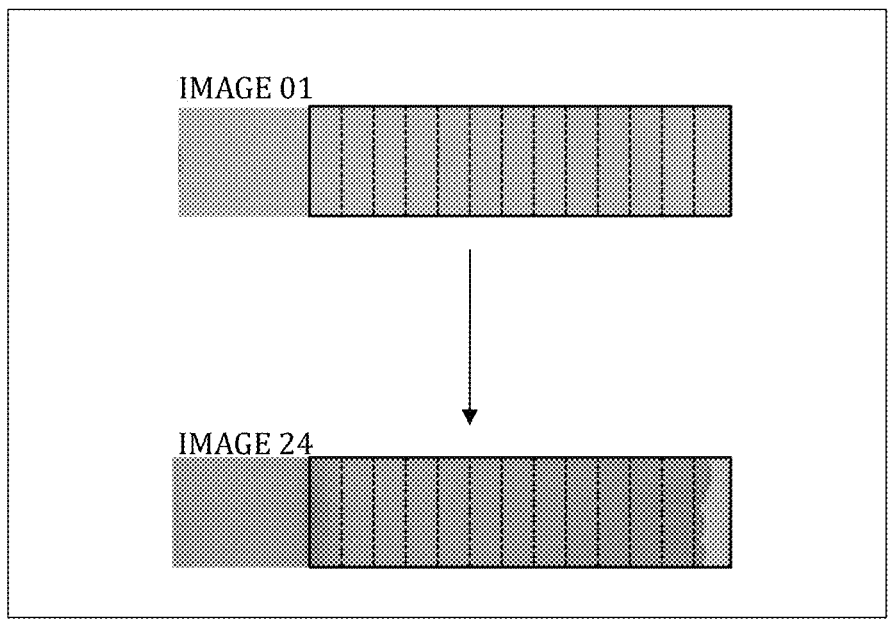
FIG. 29A is a pair of digital images of a test area, captured before and after the migration of a particle flow stream, and highlighting the subzones that comprise the capture and post-capture zones.
Figure 29B:
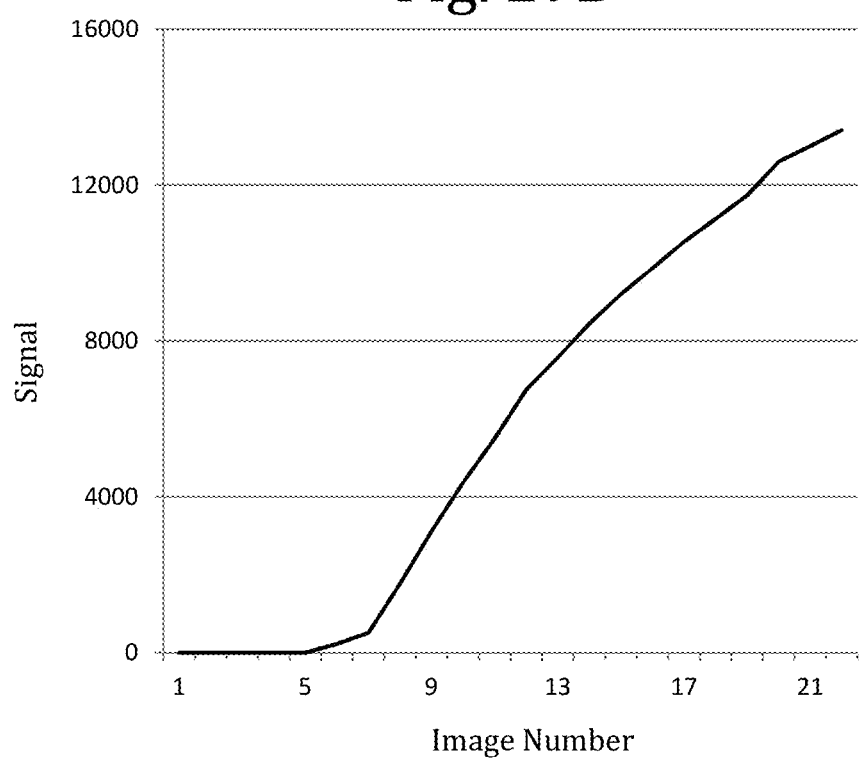
FIG. 29B is a graph plotting the total signal development (as a function of image number) in the subzones highlighted in FIG. 26A.
Figure 30:
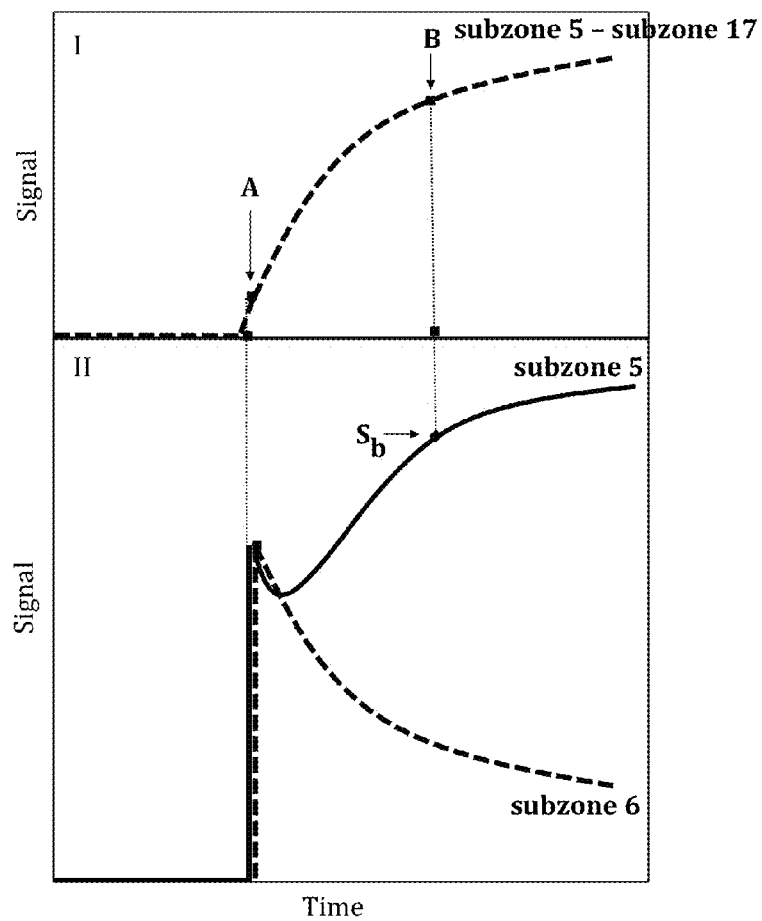
FIG. 30 is a diagrammatic representation of a graph similar to the one shown in FIG. 29B (aligned over the graph shown initially in FIG. 26) along with a legend describing spatiotemporal data points and assay parameters as depicted in the graph.

In another example of an assay parameter, total particle migration into the capture and post-capture zones is measured. FIG. 29A shows a set of digital images of a test area before particles have entered the membrane (IMAGE 1) and after the particle flow stream has migrated to a point where the front of the flow stream is about 1 mm from the end of the post-capture zone (IMAGE 24). The graph in FIG. 29B plots the total signal (summed from the 13 zones outlined in the IMAGE 24 figure) as a function of Image number. This parameter represents a direct measure of the total particle population migrated through the capture zone at any point in the assay reaction. FIG. 30 is a diagrammatic representation of the type of graph shown in FIG. 29B aligned with the type of graph shown in FIG. 26. Two data points are identified on the top graph and described in the list below the graphs. This list also notes that data point B, without additional data points or processing, qualifies as a parameter, which is directly proportional to the $S_b$ values.

FIGS. 31A-31C provides another example of a parameter usable for signal normalization. Graphs A and B were derived from the same spatiotemporal tables used in FIGS. 27A-27D, with FIG. 31A corresponding to Strip I and FIG. 31B corresponding to Strip II. The gray bar in each graph represents signal in the capture zone, while the white bars represent signal from all of the subzones in the post-capture zone. FIG. 31C shows a table comparing capture zone signals (subzone 5 minus subzone 6) in the first row and post-capture zone signals (all subzones added up) in the second row. The third row of the table shows the ratio of signal in the capture zone to signal in the post-capture zone for both strips (0.066 for strip I and 0.065 for strip II).

In a preferred embodiment, assay parameters are devised and weighted manually. In another preferred embodiment, assay parameters are devised and weighted by a computer program, such as a program that incorporates supervised machine learning.

FIGS. 32A-32C depicts an example of an unknown sample analyzed using the normalized signal calculation described in FIGS. 31A-31C. FIG. 32A shows a table with spatiotemporal data used to calculate a signal value of 0.019 for the unknown sample. FIG. 32B shows a calibration table generated from known calibration samples and stored in the analysis program. With the input signal of 0.019, the program first selects the appropriate slope and Y-intercept values from the calibration curve. Because 0.019 falls between the mean signals from the 40 and 160 calibrators (0.026 and 0.014, respectively), the slope and Y-intercept values located in the row with the 40 calibrator are selected. These values are then used in conjunction with the unknown sample signal to derive a result, using the formula: RESULT=$10^{((y-b)/m)}$ where y is the unknown sample signal, m is the slope, and b is the Y-intercept. FIG. 32C shows the values incorporated into the equation, leading to an output result of 91.7.

Example 8: Correlating Binding Signals with Assay Parameters to Generate Results (Format 2)

Example 5 demonstrated the manner in which an assay parameter could be used to normalize the binding signal in an assay reaction. In practice, the parameter would typically be combined with the binding signal through some form of mathematical operation (such as dividing one value into the other value) to create a normalized binding signal. This new value could then be used in the construction of a calibration curve, plotting normalized binding signal as a function of analyte concentration. Normalization strategies are simple and efficient when using a small number of parameters, but can become complicated when using a large number of parameters. In another preferred embodiment, assay parameters are used to classify the binding signals into multiple sets, with each set containing a separate calibration curve. The benefit of classification over normalization is that it does not require a mathematical formula to be devised relating the parameters to the binding signal, making it more convenient to work with large numbers of parameters. In addition, classification results may assist in defining complex normalization formulae.

FIG. 31A shows a diagrammatic spatiotemporal graph similar to FIGS. 27A-27D. The first box in FIG. 31B is a list of assay parameters (P1 through P3) defined from the graph. Each parameter is assigned an acceptable range of values (for example, P1 is assigned an acceptable range of 98-102) which allows the classification process to "weight" each parameter for its overall contribution to the classification (the more narrow the range, the higher the weighting). Note that while it is possible to designate units to the parameter values (delta grayscales, delta grayscales per second, etc.) these units are not necessarily required for classification. A list of weighted parameters is referred to as an "assay protocol". The second box in FIG. 31B shows a shorthand representation of the assay protocol given in the example. By assigning a parameter more than one acceptable range, multiple assay protocols are generated. Each protocol can then be associated with a discrete calibration curve template, and the protocol can serve as a unique address for that curve. Thus, by measuring a binding signal, and simultaneously measuring a protocol associated with the binding signal, the analysis program is able to group together binding signals that were generated under similar assay conditions.

FIGS. 32A-32C show a calibration curve template and demonstrates the process of populating the template with data derived from known calibration samples. FIG. 32A shows the template before any sample data has been assigned. The template indicates that the calibration curve will be generated using six known calibration levels (5, 20, 80, 320, 1280 and 5120). Note that sample units (ng/ml, mg/dl, mmol/L etc.) do not need to be applied until the final output, and can thus be stored in another location of the program. FIG. 32B represents a dataset generated from a known calibrator sample. This dataset shows three basic pieces of linked information: 1) the measured protocol showing the parameters and the measured values of the parameters (in parentheses), 2) the known analyte concentration in the sample (referred to as the "label"), and 3) the measured binding signal (referred to as the "Result"). Using the measured protocol, the program locates the appropriate template to send the dataset to. In the example note that all the parameter values in the calibration sample dataset (FIG. 31B) fall within the ranges defined by the template protocol. Having located the appropriate template, the result (95) is then placed into the appropriate row of the "Labeled Data" section based on the associated label (5). This placement is shown in FIG. 32C. After repeating the process numerous times (with sample calibrators at every level) the template becomes populated with a statistically significant number of results in the Labeled Data section (FIG. 32D). The result values are then averaged at each level and the mean is incorporated in the "Result" column of the Calibration Curve section of the template. This allows for slope and Y-intercept values to be calculated as shown in FIG. 32D (the example represents a point-to-point calibration curve). Such a completed template constitutes a defined calibration curve table which can be stored in a database of tables and used for analysis.

Figures 33A, 33B:
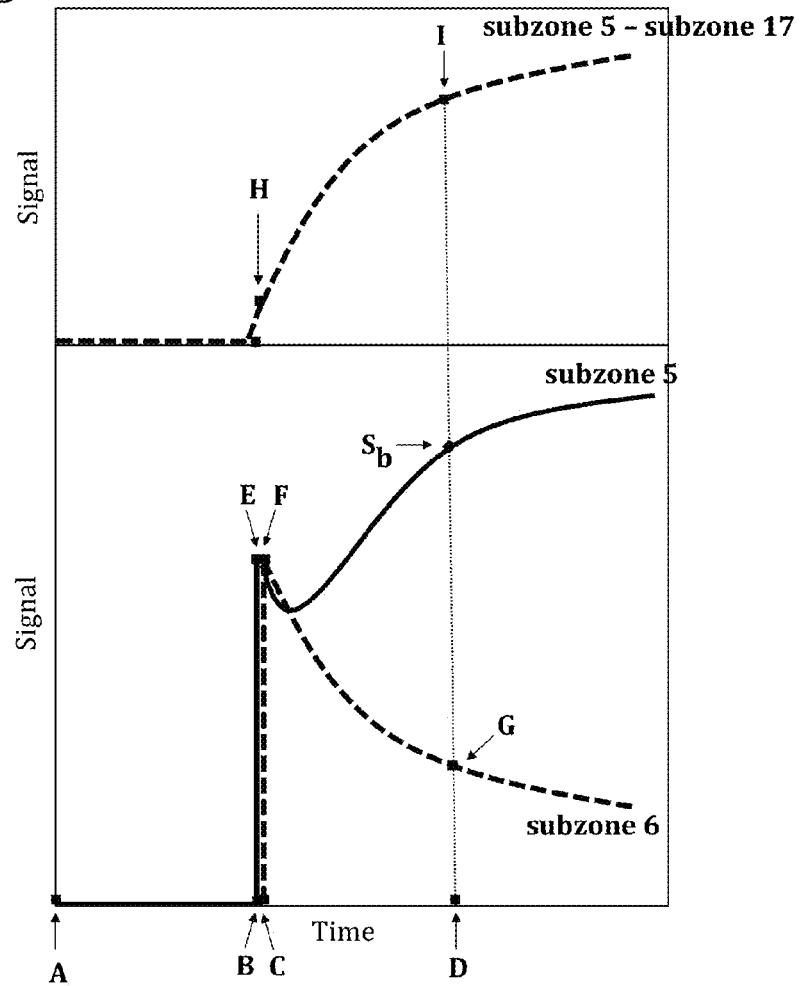
FIG. 33A is a diagrammatic representation of a graph similar to the one shown in FIG. 30.
FIG. 33B shows a first box with a list of assay parameter definitions derived from FIG. 33A along with a range of acceptable values for each parameter, and a second box showing a shorthand depiction of these ranges as a protocol address.
Figure 34:
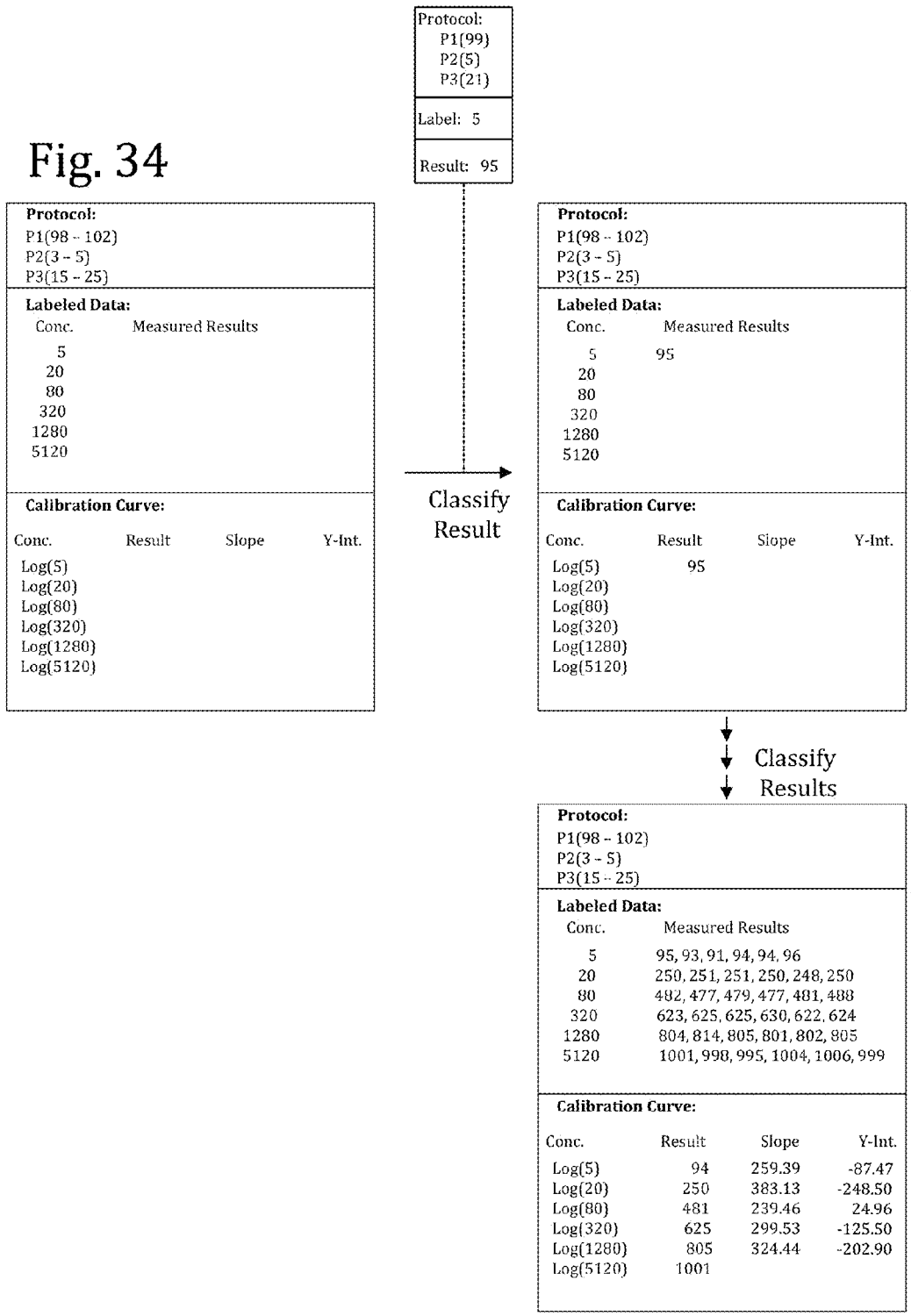
FIG. 34 depicts the process of populating a calibration curve template with data derived from known samples.
Figure 35:
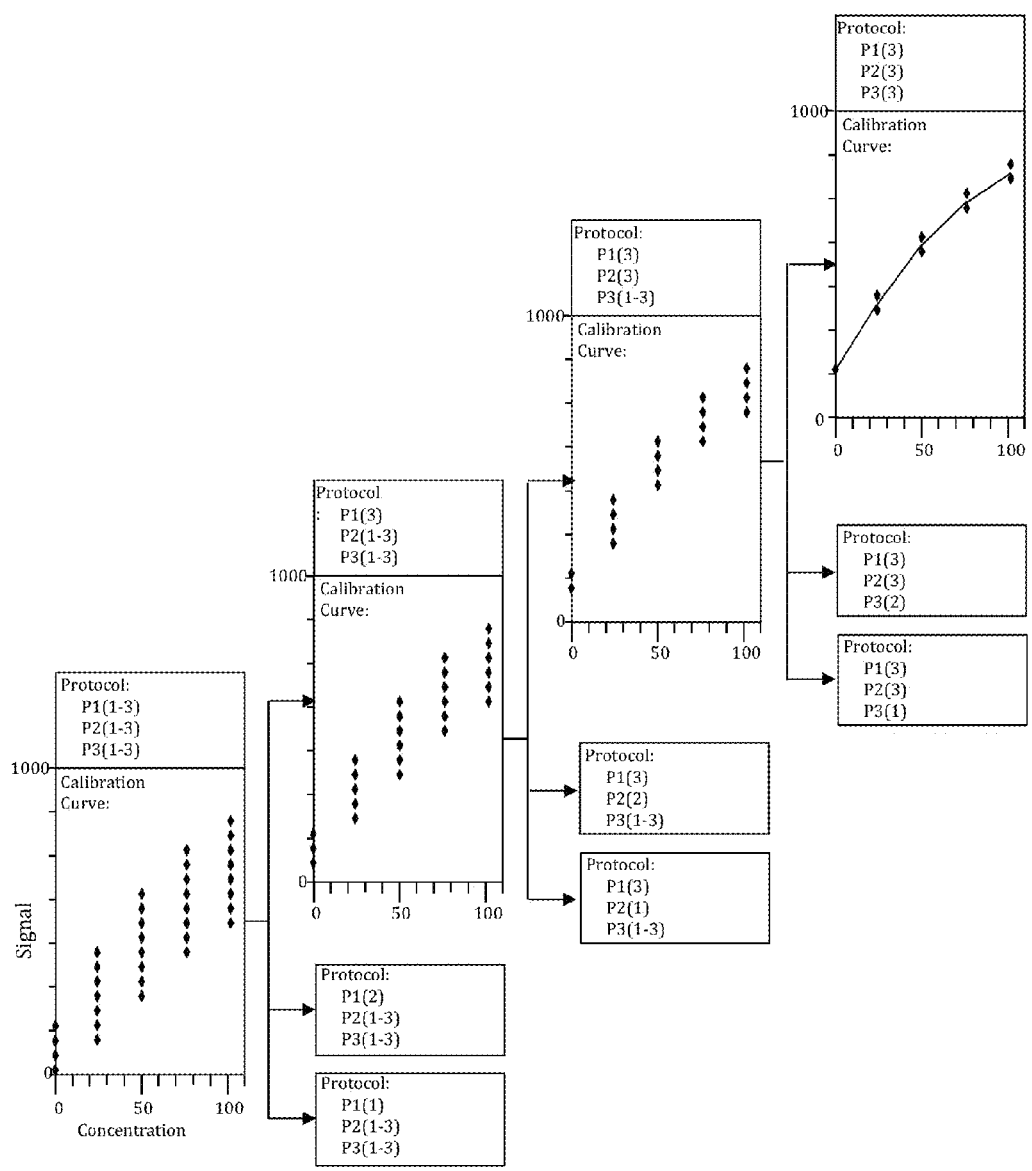
FIG. 35 depicts the process of expanding a database of calibration curve tables by narrowing the acceptable range within the assay parameters.
Figure 36:
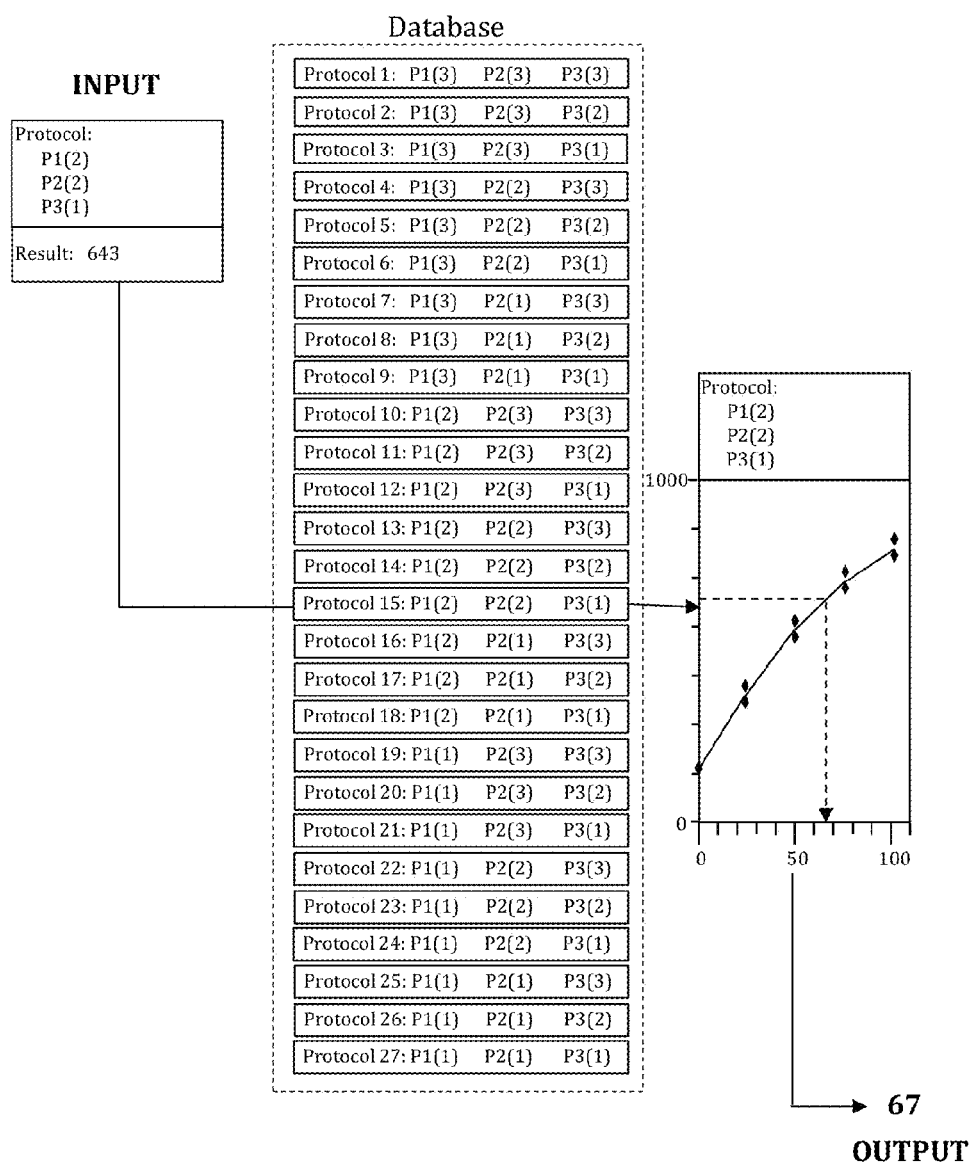
FIG. 36 shows a list of protocol addresses within a database of calibration curve tables, and depicts a process by which input data from an unknown sample matches the protocol address to locate the appropriate calibration curve for analysis.

For classification purposes, a parameter should have two or more sets of acceptable ranges covering the entire spectrum of acceptable values. For example, if the spectrum of acceptable values for a parameter is 1-12, then there may be a small number of low weighted ranges (e.g. 1-6, 7-12) a large number of high weighted ranges (e.g. 1-2, 3-4, 5-6, 7-8, 9-10, 11-12) or something in between. Broadly speaking, as parameter ranges become more highly weighted, the results in the calibration curves become less scattered, but require a larger number of calibrator samples to sufficiently populate each table. The number of tables in a database also increases with higher weighting of parameters. FIGS. 33A-33B depict a simple diagram illustrating the manner in which a database of tables is progressively built by parsing the spectrum of acceptable values into smaller ranges. The figure shows a calibration curve table similar to the one shown in FIGS. 32A-32C except that the labeled data is depicted graphically rather than in table form. The graph in the lower left portion of the figure shows a considerable amount of scatter at each concentration level owing to the low weighting of each parameter (P1(1-3), P2(1-3), P3(1-3)). As the acceptable range is sequentially narrowed for each parameter, the scatter becomes concomitantly narrowed and the number of tables in the database increases. In this simple example, the total number of tables that can be created (assuming all parameter values remain as whole numbers) is 27. FIG. 34 depict a database in which the three parameters have been maximally weighted, generated all 27 calibration curve tables. Also shown in the figure is a dataset input from an unknown sample, listing the result (643) and the three measured parameters associated with the result (P1(2), P2(2), P3(1)). With these measured parameters, the software program is able to retrieve the appropriate table (listed under Protocol 15), calculate an accurate concentration value (67) and output the result.

In a preferred embodiment, assay parameters are devised and weighted manually. In another preferred embodiment, assay parameters are devised and weighted by a computer program, such as a program that incorporates supervised machine learning.

Example 9: Correlating Binding Signals with Assay Parameters to Generate Results (Format 3)

Figure 37:
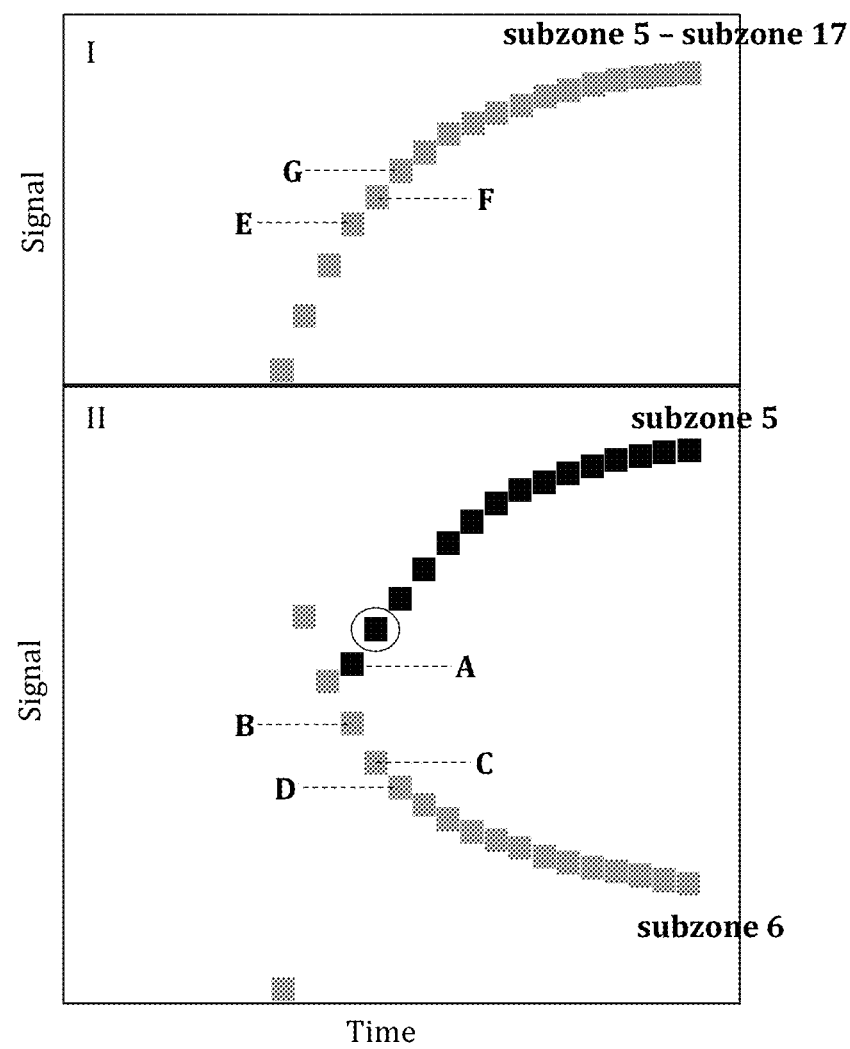
FIG. 37 is a scatterplot version of a graph similar to the one shown in FIG. 30 showing labeled data points used to define assay parameters that correlate with a circled bind curve data point.
Figure 38A:
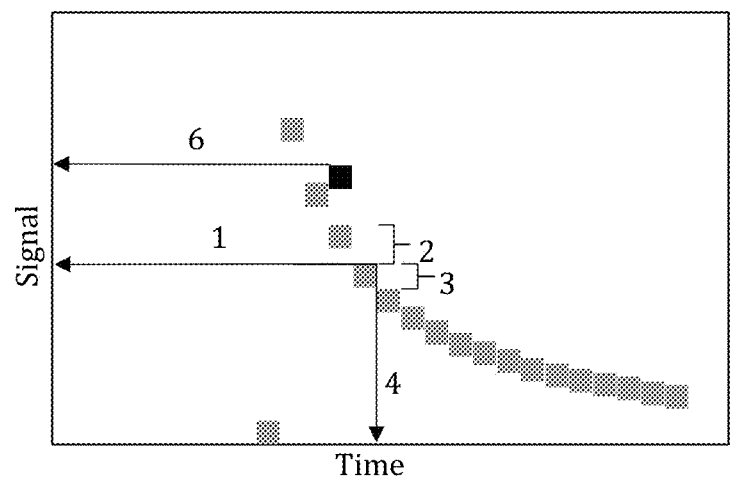
FIG. 38A shows a scatterplot graph of a flow curve wherein assay parameters are defined to calculate a bind curve data point.
Figure 38B:
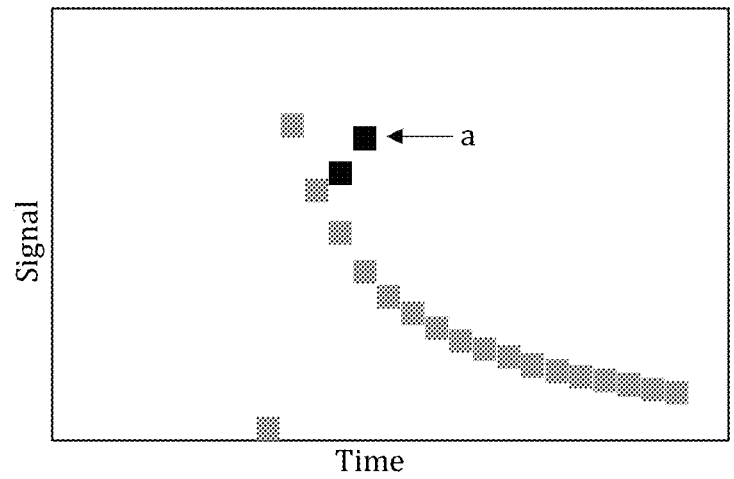
FIG. 38B shows the scatterplot graph from 38A with the calculated bind curve data point.

In Example 8, a database of multiple calibration curves, each curve linked to a set of assay parameters, was used to define the correlation between binding signals and assay parameters. Another way to correlate binding signals with assay parameters is to create a database of "calibration chunks" that link a set of measured parameters to an incremental change in the bind curve. These incremental changes could then be used to construct device-specific calibration curves in a moment-by-moment fashion, which could enable them to accommodate a wide range of variability in flow dynamics. FIG. 37 shows a diagrammatic graph of flow and bind curves similar to FIG. 30, except in this figure the curves are represented by discrete points or scatter plots rather than by lines. The figure depicts a training example produced from an assay reaction using a calibrator sample. With this dataset, each point on the bind curve can be correlated to a set of assay parameters (in this case the circled point on the bind curve is correlated to parameters linked to points A-G), and with sufficient replicates the correlations can be weighted (manually or with machine learning algorithms). Once the system has been trained, a calculated bind curve can be derived from the flow curve of a given sample. FIGS. 38A-38B depicts this process. FIG. 38A shows a set of parameter measurements taken from the flow curve and a first calculated point on the bind curve (itself calculated from points on the flow curve). These measurements are analyzed by the program to produce a second point on the bind curve (a), shown in FIG. 38B, and the process repeats itself until the full bind curve has been calculated. By applying the process to a set of calibration samples, a calibration curve can be constructed and used to analyze the bind curve produced by the sample. FIG. 39 depicts such an analysis. A sample is run on the system, producing a flow/bind curve serving as the input (Panel A). Data from the flow curve is analyzed with the calibration chunks stored in the database and a set of machine learning algorithms (Panel B) leading to the generation of a set of calculated bind curves (Panel C) used to construct a device-specific calibration curve (Panel D). Data from the bind curve of the sample is then analyzed with the calibration curve to produce a result as output (Panel E).

Example 10: Calculating Sample Matrix Binding Interference

The capture zone binding reaction of an immunochromatographic assay can be subject to non-specific interference from one or more components in a sample matrix, resulting in non-specifically reduced binding (i.e. effects on binding that are independent of analyse concentration in the sample). With conventional test systems, it is not possible to distinguish specific and non-specific binding effects. Such interferences can lead to false negative results in sandwich assays and false positive results in competitive assays.

Using the spatiotemporal analysis system described herein, a test format was designed that allowed for the detection and quantification of sample matrix interference, allowing for more accurate, precise, and reliable detection and quantification of target analytes in samples. The format was designed by first identifying a generic set of binding reagents that could be used as a reference analysis (reference reagents). These reference reagents needed to meet three criteria 1) the reference reagents must be sensitive to the same non-specific interference as the analyte-specific reagents (though not necessarily to the same degree), 2) the reference reagents must not cross-react with the target analyte to any appreciable degree, and 3) analyte for which the reference reagent is specific (non-target analyse) must have an unlikely probability of being present in any test samples at concentrations that would affect binding of the reference reagents.

The reference reagents are then configured into an assay device in such a way as to allow the reference binding reaction to be analyzed in conjunction with the analyse-specific binding reaction on a given test sample. In a preferred embodiment, the reference reagents are configured onto the same test strip as the analyte-specific reagents (in a manner similar to the incorporation of a control line in conventional strips). In another preferred embodiment, the reference reagents are configured onto a strip that is separate from the strip containing the analyte-specific reagents. These two strips may be placed in the same housing or placed in separate housings.

Using the spatiotemporal analysis system described herein, the program calculates a value (from the parameters and associated binding signal of the reference reaction) related to non-specific binding inhibition resulting from sample matrix interference. This value is then used to calculate the contribution of sample matrix inhibition on the analyte-specific binding reaction and compensate for this contribution when calculating a result.

What is claimed is:

1. A method for determining the amount of target analyte in a fluid sample, comprising:
    a) providing the fluid sample;
    b) providing a set of fluid calibrator samples containing the target analyte at defined levels;
    c) providing a plurality of assay devices, each assay device comprising a particle region incorporating test particles coated with a target analyte binding reagent and a test area incorporating a capture zone coated with the target analyte binding reagent, each assay device capable of forming, in response to an application of the fluid sample, a collection of measurable assay device compositions comprising an analyte-independent movement of the test particles through the test area and an analyte-dependent immobilization of the test particles in the capture zone, wherein the analyte-independent movement of the test particles correlates with assay parameters that define device-specific assay conditions;
    d) providing an imaging instrument operatively connected to the plurality of assay devices, wherein the imaging instrument is configured for collecting and recording each collection of measurable assay device compositions as a set of numerical spatiotemporal data points;
    e) providing a computing device operatively connected to the imaging instrument, wherein the computing device comprises an executable software program configured for analyzing each set of numerical spatiotemporal data points from the imaging instrument so as to calculate the amount of target analyte present in the fluid sample, the program using calibration processes that incorporate correlations between the assay parameters and the immobilization of the test particles in the capture zone;

f) applying one of the set of fluid calibrator samples to one of the plurality of assay devices so as to induce the formation of one collection of measurable assay device compositions;

g) collecting and recording the one collection of measurable assay device compositions of step f) on the imaging instrument to generate one set of numerical spatiotemporal data points for analysis;

h) repeating steps f) and g) for each of the set of fluid calibrator samples to induce the formation of additional collections of measureable assay device compositions, and collecting and recording the additional collections of measurable assay device compositions on the imaging instrument to create a plurality of sets of numerical spatiotemporal data points for the set of fluid calibrator samples;

i) repeating steps f), g), and h) for each of the plurality of assay devices;

j) using the software program to create a database of the plurality of sets of numerical spatiotemporal data points generated for the set of fluid calibrator samples for each of the plurality of assay devices;

k) applying the fluid sample to each of the plurality of assay devices so as to induce the formation of a plurality collection of fluid sample measurable assay device compositions;

l) collecting and recording the plurality of collection of fluid sample measurable assay device compositions of step k) on the imaging instrument to generate the fluid sample set of numerical spatiotemporal data points for analysis;

m) analyzing the fluid sample set of numerical spatiotemporal data points from step l) with the software program and the database so as to determine the amount of target analyte in the fluid sample, wherein the amount of target analyte is determined based on the amount of test particles coated with the target analyte binding reagent immobilized in the capture zone coated with the target analyte binding reagent together with the assay parameters determined from the analyte-independent movement of the particles in the test area, the assay parameters used to generate device-specific calibration.

2. The method of claim 1, wherein each assay device is an immunochromatographic assay device comprising a sample application region, the particle region containing test particles coated with the target analyte binding reagent, and the test area containing the capture zone coated with the target analyte binding reagent.

3. The method of claim 1, wherein the assay parameters that define device-specific assay conditions are selected from a group consisting of: a parameter defining the amount of test particles coated with the target analyte binding reagent that move from the particle region to the test area, a parameter defining the time required for the test particles to move from the particle region to the capture zone coated with the target analyte binding reagent, a parameter defining the time required for the test particles to traverse the capture zone, a parameter defining the total amount of test particles that traverse the capture zone at a first defined time point, and a parameter defining the instantaneous concentration of test particles in the capture zone at defined time points.

4. The method of claim 1, wherein the spatiotemporal data points are organized into a spatiotemporal table.

5. The method of claim 1, wherein the software program comprises a plurality of machine learning algorithms that use the database of the plurality of sets of numerical spatiotemporal data points as training examples to establish device-specific calibration processes.

6. The method of claim 1, wherein the the imaging instrument comprises a digital camera that records the plurality of sets of numerical spatiotemporal data points as a set of gray scale values derived from a succession of digital images of the test area captured over time.

* * * * *